Figure 1:
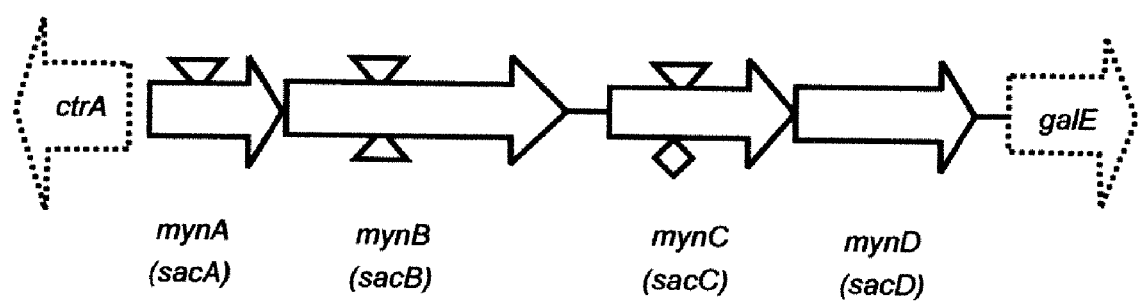

US007883876B2

(12) United States Patent
Stephens et al.

(10) Patent No.: US 7,883,876 B2
(45) Date of Patent: Feb. 8, 2011

(54) ***NEISSERIA MENINGITIDIS* SEROGROUP A CAPSULAR POLYSACCHARIDE ACETYLTRANSFERASE, METHODS AND COMPOSITIONS**

(76) Inventors: David S. Stephens, 5221 Gauley River Dr., Stone Mountain, GA (US) 30087; Seshu K. Gudlavalleti, 3905 Halsey St., Kensington, MD (US) 20895; Yih-Ling Tzeng, 2969 Dale Dr., Atlanta, GA (US) 30305; Anup K. Datta, 8510 Costa Verde Blvd., San Diego, CA (US) 92122; Russell W. Carlson, 104 Goddard Rd., Athens, GA (US) 30607

( * ) Notice: Subject to any disclaimer, the term of this patent is extended or adjusted under 35 U.S.C. 154(b) by 509 days.

(21) Appl. No.: 11/943,326

(22) Filed: Nov. 20, 2007

(65) Prior Publication Data

US 2009/0208533 A1 Aug. 20, 2009

Related U.S. Application Data

(62) Division of application No. 11/201,774, filed on Aug. 11, 2005, now abandoned.

(60) Provisional application No. 60/600,862, filed on Aug. 11, 2004.

(51) Int. Cl.
*C12P 19/04* (2006.01)
*A61K 39/095* (2006.01)

(52) U.S. Cl. .................. 435/101; 424/250.1; 424/279.1

(58) Field of Classification Search ....................... None
See application file for complete search history.

(56) References Cited

U.S. PATENT DOCUMENTS

| | | | |
|---|---|---|---|
| 3,817,837 | A | 6/1974 | Rubenstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |
| 4,683,195 | A | 7/1987 | Mullis et al. |
| 4,683,202 | A | 7/1987 | Mullis et al. |
| 4,800,159 | A | 1/1989 | Mullis et al. |
| 4,816,567 | A | 3/1989 | Cabilly et al. |
| 5,976,536 | A | 11/1999 | Stephens et al. |
| 6,403,306 | B1 | 6/2002 | Stephens et al. |
| 2005/0106184 | A1 | 5/2005 | Franks et al. |
| 2006/0073168 | A1 | 4/2006 | Stephens et al. |

FOREIGN PATENT DOCUMENTS

| | | | |
|---|---|---|---|
| WO | WO 93/16094 A2 | 8/1993 | |
| WO | WO 9845312 A1 | 10/1998 | |
| WO | WO 03/079995 | 10/2003 | |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Altschul et al., "Basic local alignment search tool," Oct. 5,1990 *J. Mol. Bio.* 215(3):403-410.
Altschul et al., "Gapped BLAST and PSI-BLAST: a new generation of protein database search programs," Sep. 1, 1997 *Nuc. Acids Res.* 25(17):3389-3402.
Antignac et al., "*Neisseria meningitidis* strains isolated from invasive infections in France (1999-2002): phenotypes and antibiotic susceptibility patters," Oct. 1, 2003 *Clin. Infect. Dis.* 37(7):912-920. Available online on Sep. 9, 2003.
Ausubel et al. (eds.), *Current Protocols in Molecular Biology*, vols. 1-4, John Wiley & Sons, Inc.: New York, NY; 1995. Cover page, publisher's page and table of contents.
Beaucage and Caruthers, "Deoxynucleoside phosphoramidites—A new class of key intermediates for deoxypolynucleotide synthesis," 1981 *Tetra. Letters* 22(20):1859-1862.
Beltz et al., in *Methods of Enzymology*, vol. 100 (Wu et al., Eds.). Academic Pres: New York, NY; 1983. Cover page, publisher's page and pp. 266-285.
Bloemberg et al., "Nodulation protein NodL of *Rhizobium leguminosarum* O-acetylates lipo-oligosaccharides, chitin fragments and N-acetylglucosamine in vitro," Feb. 1994 *Mol. Microbiol.* 11(4):793-804.
Campos et al., "Genetic diversity of penicillin-resistant *Neisseria meningitidis*," Jul. 1992 *J. Infect. Dis.* 166(1):173-177.
Caugant et al., "Intercontinental spread of a genetically distinctive complex of clones of *Neisseria meningitidis* causing epidemic disease," Jul. 1986 *PNAS* 83(13):4927-4931.
Caugant et al., "Genetic structure of *Neisseria meningitidis* population in relation to serogroup, serotype, and outer membrane protein pattern," Jun. 1987 *J. Bacteriol.* 169(6):2781-2792.
Center for Disease Control, "Serogroup B meningococcal Disease—Oregon, 1994" Feb. 24, 1995 *MMWR* 44(7):121-134. Available online [retrieved on Aug. 21, 2009]. Retrieved from the Internet: <http://www.cdc.gov/mmwr/preview/mmwrhtml/00035870.1nni>; 5 pgs.
Dayhoff et al., "A model of evolutionary change in proteins," in *Atlas of Protein Sequence and Structure*, vol. 5, Supplement 3. The National Biomedical Research Foundation: Silver Spring, MD; 1979. Cover page, publisher's page, and pp. 345-352.
deMaagd and Lugtenberg, "Fractionation of *Rhizobium leguniinosarum* cells into outer membrane, cytoplasmic membrane, periplasmic, and cytoplasmic components," Sep. 1986 *J. Bacteriol.* 167(3):1083-1085.

(Continued)

*Primary Examiner*—N. M. Minnifield
*Assistant Examiner*—Brian J Gangle
(74) *Attorney, Agent, or Firm*—Mueting Raasch & Gebhardt, P.A.

(57) ABSTRACT

Provided are methods for recombinant production of an O-acetyltransferase and methods for acetylating capsular polysaccharides, especially those of a Serogroup A *Neisseria meningitidis* using the recombinant O-acetyltransferase, and immunogenic compositions comprising the acetylated capsular polysaccharide.

20 Claims, 14 Drawing Sheets

OTHER PUBLICATIONS

Denk and Bock, "L-cysteine biosynthesis in *Escherichia coli*: nucleotide sequence and expression of the serine acetyltransferase (cysE) gene from the wild-type and a cysteine-excreting mutant," Mar. 1987 *J. Gen. Microbiol.* 133(3):515-525.

Dorsey et al., "Genetic organization of an *Acinobacter baumannii* chromosomal region harbouring genes related to siderophore biosynthesis and transport," May 2003 *Microbiology* 149(Pt 5):1227-1238.

Drogari-Apiranthitou et al., "Complement activation and formation of the membrane attack complex on serogroup B *Neisseria meningitidis* in the presence or absence of serum bactericidal activity," Jul. 2002 *Infect. Immun.* 70(7):3752-3758.

Dubois et al., "Colorimetric method for determination of sugars and related substances," Mar. 1956 *Anal. Chem.* 28(3):350-356.

Finberg et al., "Interactions of VirB9, -10, and -11 with the membrane fraction of *Agrobacterium tumefaciens*: solubility studies provide evidence for tight associations," Sep. 1995 *J. Bacteriol.* 177(17):4881-4889.

Georgia Research Foundation, University of Georgia, "New Award—The Center for Plant and Microbial Complex Carbohydrates at the University of Georgia Complex Carbohydrate Research Center,", Contract No. DE-FG02-93ER20097 [online]. United States Department of Energy Office of Science. Project dates Dec. 16, 1992 to Dec. 31, 2012 [retrieved on Aug. 26, 2009]. Retrieved from the Internet: <http://www.osti.gov/rdprojects/details.jsp?query_id=P/CH--FG02-93ER20097>; 2 pgs.

Girardin et al., "Peptidoglycan molecular requirements allowing detection by Nod1 and Nod2," Oct. 24, 2003 *J. Biol. Chem.* 278(43):41702-41708. Available online on Jul. 8, 2003.

Glover (Ed.), *DNA Cloning vol. I a practical approach*. IRL Press: Oxford, England; 1985. Cover page, publisher's page, and table of contents.

Glover (Ed.), *DNA Cloning vol. II: a practical approach*. IRL Press: Oxford, England; 1985. Cover page, publisher's page, and table of contents.

Goding, *Monoclonal Antibodies: Principles and Practice, 2nd Edition*. Academic Press: New York, NY; 1986. Cover page, publisher's page and table of contents.

Grossman and Moldave (Eds.), *Methods in Enzymology vol. 65: Nucleic Acids Part I*. Academic Press: New York, NY; 1980. Cover page, publisher's page and table of contents.

Hames and Higgens (eds.), *Nucleic Acid Hybridisation: a practical approach*. IRL Press Limited: Oxford, England; 1985. Cover page, publisher's page, and table of contents.

Hanahan, "Studies on transformation of *Escherichia coli* with plasmids," Jun. 5, 1983 *J. Mol. Biol.* 166(4):557-580.

Hara and Hutchinson, "A macrolide 3-O-acytransferase gene from the midecamycin-producing species *Streptomyces mycarofaciens*," Aug. 1992 *J. Bacteriol.* 174(15):5141-5144.

Harlow et al., *Antibodies: A Laboratory Manual*, Cold Spring Harbor Laboratory Press: Cold Spring Harbor, NY; 1988. Cover page, publisher's page, and table of contents only.

Hestrin, "The reaction of acetylcholine and other carboxylic acid derivatives with hydroxylamine, and its analytical application," Aug. 1949 *J. Biol. Chem.* 180(1):249-261.

Hindson et al., "Serine acetyltransferase from *Escherichia coli* is a dimer of trimers," Jan. 7, 2000 *J. Biol. Chem.* 275(1):461-466.

Hindson et al., "Kinetic and hydrodynamic studies on the NodL O-acetyl transferase of *Rhizobium leguminosarum*: a random-order ternary complex mechanism for acetyl transfer by a roughly spherical trimeric protein," Jun. 15, 2000 *Biochim. Biophys. Acta* 1479(1-2):203-213.

Inohara et al., "Host recognition of bacterial muramyl dipeptide mediated through NOD2. Implications for Crohn's disease," Feb. 21, 2003 *J. Biol. Chem.* 278(8):5509-5512. Available online on Jan. 4, 2003.

Jackson et al., "Serogroup C meningococcal outbreaks in the United States: an emerging threat," Feb. 1, 1995 *JAMA* 273(5):383-389.

Jennings et al., "Structures of the capsular polysaccharides of *Neisseria meningitidis* as determined by 13C-nuclear magnetic resonance spectroscopy," Aug. 1977 *J. Infect. Dis.* 136(Supp):S78-S83.

Karlin and Altschul, "Methods for assessing the statistical significance of molecular sequence features by using general scoring schemes," Mar. 1990 *PNAS* 87(6):2264-2268.

Karlin and Altschul, "Applications and statistics for multiple high-scoring segments in molecular sequences," Jun. 15, 1993 *PNAS* 90(12):5873-5877.

Keller and Manak, "Hybridization of filters with radiolabeled probes," in *DNA Probes* Stockton Press: New York, NY; 1989. Cover page, publisher's page and pp. 169-170.

Krizova and Musilek, "Changing epidemiology of meningococcal invasive disease in the Czech republic caused by new clone *Neisseria meningitidis* C:2a:P1.2(P1.5), ET-15/37," Nov. 1995 *Centr. Eur. J Publ. Health* 3(5):189-194.

Larionov and Nikiforov, "Directed mutagenesis," March 1982 *Genetika* 18(3):349-359. English language summary included.

Lewendon et al., "Structural and mechanistic studies of galactoside acetyltransferase, the *Escherichia coli* LacA gene product," Nov. 3, 1995 *J. Biol. Chem.* 270(44):26326-26331.

Lopez-Lara et al., "Structural identification of the lipo-chitin oligosaccharide nodulation signals of *Rhizobium loti*," Feb. 1995 *Mol. Microbiol.* 15(4):627-638.

Amir et al. (2005) "Naturally-Acquired Immunity to *Neisseria meningitidis* Group A," *Vaccine* 23:977-983.

Berry et al. (2002) "Effect of O Acetylation of *Neisseria meningitidis* Serogroup A Capsular Polysaccharide on Development of Functional Immune Responses," *Infect. Immun.* 70:3701-3713.

Bhasin et al. (1998) "Identification of a Gene Essential for O-Acetylation of the *Staphylococcus aureus* Type 5 Capsular Polysaccharide," *Mol. Microbiol.* 27:9-21.

Bhattacharjee et al. (1975) "Structural Determination of the Sialic Acid Polysaccharide Antigens of *Neisseria meningitidis* Serogroups B and C with Carbon 13 Nuclear Magnetic Resonance," *J. Biol. Chem.* 250:1926-1932.

Bhattacharjee et al. (1976) "Structural Determination of the Polysaccharide Antigens of *Neisseria meningitidis* Serogroups Y, W-135, and BO," *Can. J. Biochem.* 54:1-8.

Bundle et al. (1974) "Determination of the Structure and Conformation of Bacterial Polysaccharides by Carbon 13 Nuclear Magnetic Resonance," *J. Biol. Chem.* 249:2275-2281.

Clark et al. (1987) "Induction and Repression of Outer Membrane Proteins by Anaerobic Growth of *Neisseria gonorrhoeae*," *Infect. Immun.* 55:1359-1364.

Claus et al. (Jan. 2004) "Genetics of Capsule O-Acetylation in Serogroup C, W-135 and Y Meningococci," *Mol. Microbiol.* 51:227-239.

Fattom et al. (1998) "Antigenic Determinants of *Staphylococcus aureus* Type 5 and Type 8 Capsular Polysaccharide Vaccines," *Infect. Immun.* 66:4588-4592.

Filice et al. (1985) "Risk of Group A Meningococcal Disease: Bacterial Interference and Cross-Reactive Bacteria Among Mucosal Flora," *J. Clin. Microbiol.* 22:152-156.

Firmin et al. (1993) "Resistance to Nodulation of cv. Afghanistan Peas is Overcome by *nodX*, Which Mediates an O-Acetylation of the *Rhizobium leguminosarum* Lipo-Oligosaccharide Nodulation Factor," *Mol. Microbiol.* 10:351-360.

Franklin et al. (2002) "Mutant Analysis and Cellular Localization of the AlgI, AlgJ, and AlgF Proteins Required for O Acetylation of Alginate in *Pseudomonas aeruginosa*," *J. Bacteriol.* 184:3000-3007.

Glick et al. (1994) "Molecular Biotechnology, Principles and Applications of Recombinant DNA", ASM Press, p. 90-91.

Gotschlich et al. (1969) "Human Immunity to the Meningococcus," *J. Exp. Med.* 129:1349-1365.

Gudlavalleti et al. (Oct. 2004) "The *Neisseria meningitidis* Serogroup A Capsular Polysaccharide O-3 and O-4 Acetyltransferase," *J. Biol. Chem.* 279:42765-42773.

Higa et al. (1988) "Acetyl-Coenzyme A: Polysialic Acid O-Acetyltransferase from K1-Positive *Escherichia coli*," *J. Biol. Chem.* 263:8872-8878.

Janik et al. (1976) Genetic Transformation as a Tool for Detection of *Nesseria gonorrhoeae*, *J. Clin. Microbiol.* 4:71-81.

Jones et al. (2002) "Use and Validation of NMR Assays for the Identity and O-Acetyl Content of Capsular Polysaccharides From *Neisseria meningitidis* Used in Vaccine Manufacture," *J. Pharm. Biomed. Anal.* 30:1233-1247.

Kahler et al. (1998) "The ($\alpha 2 \rightarrow 8$)-Linked Polysialic Acid Capsule and Lipooligosaccharide Structure Both Contribute to the Ability of Serogroup B *Neisseria meningitidis* to Resist the Bactericidal Activity of Normal Human Serum," *Infect. Immun.* 66:5939-5947.

Karlyshev et al. (2000) "Genetic and Biochemical Evidence of a *Campylobacter jejuni* Capsular Polysaccharide that Accounts for Penner Serotype Specificity," *Mol. Microbiol.* 35:529-541.

Kaeberlein et al. (2002) "Isolating 'Uncultivable' Microorganisms in Pure Culture in a Simulated Natural Environment," Science, 296:1127-1129.

Kroon et al. (2000) "A Modular Esterase from *Penicillium funiculosum* Which Releases Ferulic Acid from Plant Cell Walls and Binds Crystalline Cellulose Contains a Carbohydrate Binding Module," *Eur. J. Biochem.* 267:6740-6752.

Lemercinier et al. (1996) "Full $^1$H NMR Assignment and Detailed O-Acetylation Patterns of Capsular Polysaccharides from *Neisseria meningitidis* Used in Vaccine Production," *Carbohydr. Res.* 296:83-96.

Liu et al. (1971) "Studies on the Meningococcal Polysaccharides. I. Composition and Chemical Properties of the Group A Polysaccharide," *J. Biol. Chem.* 246:2849-2858.

Liu et al. (1971) "Studies on the Meningococcal Polysaccharides. II. Composition and Chemical Properties of the Group B and C Polysaccharide,", *J. Biol. Chem.* 246:4703-4712.

Longworth et al. (2002) "O-Acetylation Status of the Capsular Polysaccharides of Serogroup Y and W135 Meningococci Isolated in the UK," *FEMS Immunol. Med. Microbiol.* 32:119-123.

Luck et al. (2001) "A Point Mutation in the Active Site of *Legionella pneumophila* O-Acetyltransferase Results in Modified Lipopolysaccharide But Does Not Influence Virulence," *Int. J. Med. Microbiol.* 291:345-352.

Luthi et al. (1990) "Cloning, Sequence Analysis, and Expression of Genes Encoding Xylan-Degrading Enzymes from the Thermophile 'Caldocellum saccharolyticum'," *Appl. Environ. Microbiol.* 56:1017-1024.

McNeely et al. (1998) "Antibody Responses to Capsular Polysaccharide Backbone and O-Acetate Side Groups of *Streptococcus pneumoniae* Type 9V in Humans and Rhesus Macaques," *Infect. Immun.* 66:3705-3710.

Nivens et al. (2001) "Role of Alginate and Its O Acetylation in Formation of *Pseudomonas aeruginosa* Microcolonies and Biofilms," *J. Bacteriol.* 183:1047-1057.

Orskov et al. (1979) "Form Variation in *Escherichia coli* K1: Determined by O-Acetylation of the Capsular Polysaccharide," *J. Exp. Med.* 149:669-685.

Parkhill et al. (2000) "Putative Capsule Biosynthesis Protein," NCBI Accession No. CAB83515.

Pier et al. (2001) "Role of Alginate O Acetylation in Resistance of Mucoid *Pseudomonas aeruginosa* to Opsonic Phagocytosis," *Infect. Immun.* 69:1895-1901.

Pinner et al. (1992) "Epidemic Meningococcal Disease in Nairobi, Kenya, 1989," *J. Infect. Diseases* 166:359-364.

Richmond et al. (2001) "Evaluation of De-O-Acetylated Meningococcal C Polysaccharide-Tetanus Toxoid Conjugate Vaccine in Infancy: Reactogenicity, Immunogenicity, Immunologic Priming, and Bactericidal Activity Against O-Acetylated and De-O-Acetylated Serogroup C Strains," *Infect. Immun.* 69:2378-2382.

Richmond et al. (1999) "Safety and Immunogenicity of a New *Neisseria meningitidis* Serogroup C-Tetanus Toxoid Conjugate Vaccine in Healthy Adults," *Vaccine* 18:641-646.

Sassenfeld (1990) "Engineering Proteins for Purification," Trends Biotech. 8:88-93.

Sau et al. (1997) "Molecular Characterization and Transcriptional Analysis of Type 8 Capsule Genes in *Staphylococcus aureus*," *J. Bacteriol.* 179:1614-1621.

Slauch et al. (1996) "Molecular Characterization of the *oafA* Locus Responsible for Acetylation of *Salmonella typhimurium* O-Antigen: OafA Is a Member of a Family of Integral Membrane Trans-Acylases," *J. Bacteriol.* 178:5904-5909.

Stephens et al. (1983) "Interaction of *Neisseria meningitidis* With Human Nasopharyngeal Mucosa: Attachment and Entry into Columnar Epithelial Cells," *J. Infect. Dis.* 148:369-376.

Stevenson et al. (1991) "Chemical Methods for the Analysis of Sulphated Galactans from Red Algae," *Carbohydr. Res.* 210:277-298.

STIC sequence search, pp. 1-2, Sep. 2006.

Swartley et al. (1998) "Characterization of the Gene Cassette Required for Biosynthesis of the ('1→6)-Linked N-Acetyl-D-Mannosamine-1-Phosphate Capsule of Serogroup A *Neisseria meningitidis*," *J. Bacteriol.* 180:1533-1539.

Szu et al. (1991) "Relation Between Structure and Immunologic Properties of the Vi Capsular Polysaccharide," *Infect. Immun.* 59:4555-4561.

Szymanski et al. (Jul. 2003) "Detection of Conserved N-Linked Glycans and Phase-Variable Lipooligosaccharides and Capsules from Campylobacter Cells by Mass Spectrometry and High Resolution Magic Angle Spinning NMR Spectroscopy," *J. Biol. Chem.* 278:24509-24520.

Tzeng et al. (2002) "Endotoxin of *Neisseria meningitidis* Composed Only of Intact Lipid A: Inactivation of the Meningococcal 3-Deoxy-D-Manno-Octulosonic Acid Transferase," *J. Bacteriol.* 184:2379-2388.

Verma et al. (1991) "Molecular Characterization of the O-Acetyl Transferase Gene of Converting Bacteriophage SF6 that Adds Group Antigen 6 to *Shigella flexneri*," *Mol. Microbiol.* 5:71-75.

Yi et al. (Apr. 2003) "Development and Evaluation of an Improved Mouse Model of Meningococcal Colonization," *Infect. Immun.* 71:1849-1855.

Zollinger et al. (1987) "Human Bactericidal Antibody Response to Menigococcal Outer Membrane Protein Vaccines," *Antonie Van Leeuwenhoek* 53:403-411.

Zollinger et al. (1991) "Meningococcal Vaccines—Present and Future," *Trans. R. Soc. Trop. Med. Hyg.* 85(Supp. 1):37-43.

Office Actions and Responses from U.S. Appl. No. 11/201,774 filed Aug. 11, 2005.

Apicella, "189. *Neisseria meningitidis*," in *Principles and Practice of Infectious Diseases Fourth Edition* (Mandell et al., Eds.). Churchill Livingstone, NY; 1995. Cover page, publisher's page, and pp. 1896-1909.

Maniatis (Ed.), *Molecular Cloning: A Laboratory Manual*. Cold Spring Harbor Press: Cold Spring Harbor, NY; 1982. Cover page, publisher's page and pp. 135-139.

Matteuci and Caruthers, "Synthesis of deoxyoligonucleotides on a polymer support," Jun. 1981 *J. Am. Chem. Soc.* 103(11):3185-3191.

Menard et al., "Nonpolar mutagenesis of the ipa genes defines IpaB, IpaC, and IpaD as effectors of *Shigella flexneri* entry into epithelial cells," Sep. 1993 *J. Bacteriol.* 175(18):5899-5906.

Metzger et al., "The human oestrogen receptor functions in yeast," Jul. 7, 1988 *Nature* 334(6177):31-36.

Miller (Ed.), *Experiments in Molecular Genetics*, Cold Spring Harbor Laboratory Press: Cold Spring Harbor, NY; 1972. Cover page, publisher's page and table of contents.

National Center for Biotechnology Information, National Library of Medicine, National Institutes of Health, Entrez Protein Locus CAB83515, Accession No. CAB83515, "putative capsule biosynthesis protein [*Neisseria meningitidis* Z2491]," [online]. Bethesda, MD [retrieved on Aug. 4, 2005]. Retrieved from the Internet: <http://www.ncbi.nlm.nih.gov/entrez/viewer.fcgi?db=protein&val=7378970>; 2 pgs.

National Center for Biotechnology Information, National Library of Medicine, National Institutes of Health, Entrez Protein Locus NP_283048, Accession No. NP_283048, "Capsule biosynthesis protein [*Neisseria meningitidis* Z2491]," [online]. Bethesda, MD [retrieved on Aug. 11, 2005]. Retrieved from the Internet: <http://www.ncbi.nlm.nih.gov/entrez/viewer.fcgi?db=protein&val=15793226>; 2 pgs.

Old and Primrose, *Principles of Gene Manipulation: an introduction to genetic engineering*. University of California Press: Berkeley, CA; 1981. Cover page, publisher's page, and table of contents.

Reuhs et al., "*Rhizobium fredii* and *Rhizobium meliloti* produce 3-deoxy-D-manno-2-octulosonic acid-containing polysaccharides that are structurally analogous to group II K antigens (capsular polysaccharides) found in *Escherichi coli*," Jun. 1993 *J Bacteriol.* 175(11):3570-3580.

Roberts, "The biochemistry and genetics of capsular polysaccharide production in bacteria," 1996 *Ann. Rev. Microbiol.* 50:285-315.

Roberts, "An ill wind, bringing meningitis," Jun. 27, 2008 *Science* 320(5884):1710-1715.

Roberts, "Hitting early, epidemic meningitis ravages Nigeria and Niger," Apr. 3, 2009 *Science* 324(5923):20-21.

Sacchi et al., "Characterization of epidemic *Neisseria meningitidis* serogroup C strains in several Brazilian states," Jul. 1994 *J Clin. Microbiol.* 32(7):1783-1787.

Saiki et al., "Enzymatic amplification of beta-globin genomic sequences and restriction site analysis for diagnosis of sickly cell anemia," Dec. 20, 1985 *Science* 230(4723):1350-1354.

Sambrook et al., *Molecular Cloning: A Laboratory Manual, Books 1-3*, Cold Spring Harbor Laboratory Press: Cold Spring Harbor, NY; 1989. Cover page, publisher's page and table of contents.

Schleif and Wensink, *Practical Methods in Molecular Biology.* Springer-Verlag:New York, NY; 1982. Cover page, publisher's page, and table of contents.

Setlow and Hollaender, *Genetic Engineering: Principles and Methods, vols. 1-4.* Plenum Press: New York, NY; 1979. Cover page, publisher's page, and table of contents.

Shortie et al., "Directed mutagenesis," 1981 *Ann. Rev. Genet.* 15:265-294.

Spaink et al., "A novel highly unsaturated fatty acid moiety of lipo-oligosaccharide signals determines host specificity of *Rhizobium*," Nov. 14, 1991 *Nature* 354(6349):125-130.

Stephans, David, "Regulation of capsule biosynthesis in *N. meningitidis*," Grant No. 1R21AI040247-01 [online]. National Institute of Allergy and Infectious Diseases, National Institutes of Health. Project dates Sep. 1, 1996 to Jul. 30, 1998 [retrieved on Aug. 21, 2009]. Retrieved from the Internet: <http://crisp.cit.nih.gov/crisp/CRISP_LIB.getdoc?textkey=2077134&p_grant_num=1R21AI040247-01A1&p_query=&ticket=103024486&p_audit_session_id=490423252&p_keywords=>; 1 pg. Title only.

Stephans, David, "Regulation of capsule biosynthesis in *N. meningitidis*," Grant Abstract, Grant No. 1RO1AI040247-01A1 [online]. National Institute of Allergy and Infectious Diseases, National Institutes of Health. Project dates Jul. 1, 1997 to Jun. 30, 2001 [retrieved on Aug. 21, 2009]. Retrieved from the Internet: <http://crisp.cit.nih.govicrisp/CRISP_LIB.getdoc?textkey=2004918&p_grant_num=1R01AI040247-01A1&p_query=&ticket=103024486&p_audit_session_id=490423252&p_keywords=>; 2 pgs.

Stephans, David, "Regulation of capsule biosynthesis in *N. meningitidis*," Grant Abstract, Grant No. 5RO1AI040247-02 [online]. National Institute of Allergy and Infectious Diseases, National Institutes of Health. Project dates Jul. 1, 1997 to Jun. 30, 2001 [retrieved on Aug. 21, 2009]. Retrieved from the Internet: <http://crisp.cit.nih.gov/crisp/CRISP_LIB.getdoc?textkey=2672841&p_grant_num=5R01AI040247-02&p_query=&ticket=103024486&p_audit_session_id=490423252&p_keywords=>; 2 pgs.

Stephans, David, "Regulation of capsule biosynthesis in *N. meningitidis*," Grant Abstract, Grant No. 5RO1AI040247-03 [online]. National Institute of Allergy and Infectious Diseases, National Institutes of Health. Project dates Jul. 1, 1997 to Jun. 30, 2001 [retrieved on Aug. 21, 2009]. Retrieved from the Internet: <http://crisp.cit.nih.gov/crisp/CRISP_LIB.getdoc?textkey=2887278&p_grant_num=5R01AI040247-03&p_query=&ticket=103024486&p_audit_session_id=490423252&p_keywords=>; 2 pgs.

Stephans, David, "Regulation of capsule biosynthesis in *N. meningitidis*," Grant Abstract, Grant No. 5RO1AI040247-04 [online]. National Institute of Allergy and Infectious Diseases, National Institutes of Health. Project dates Jul. 1, 1997 to Feb. 28, 2002 [retrieved on Aug. 21, 2009]. Retrieved from the Internet: <http://crisp.cit.nih.gov/crisp/CRISP_LIB.getdoc?textkey=6170270&p_grant_num=5R01AI040247-04&p_query=&ticket=103024486&p_audit_session_id=490423252&p_keywords=>; 2 pgs.

Stephans, David, "Regulation of capsule biosynthesis in *N. meningitidis*," Grant Abstract, Grant No. 5RO1AI040247-05A1 [online]. National Institute of Allergy and Infectious Diseases, National Institutes of Health. Project dates Jul. 1, 1997 to Feb. 28, 2002 [retrieved on Aug. 21, 2009]. Retrieved from the Internet: <http://crisp.cit.nih.gov/crisp/CRISP_LIB.getdoc?textkey=6477828&p_grant_num=2R01AI040247-05A1&p_query=&ticket=103024486&p_audit_session_id=490423252&p_keywords=>; 2 pgs.

Stephans, David, "Regulation of capsule biosynthesis in *N. meningitidis*," Grant Abstract, Grant No. 5RO1AI040247-06 [online]. National Institute of Allergy and Infectious Diseases, National Institutes of Health. Project dates Jul. 1, 1997 to Feb. 28, 2002 [retrieved on Aug. 21, 2009]. Retrieved from the Internet: <http://crisp.cit.nih.gov/crisp/CRISP_LIB.getdoc?textkey=6614451&p_grant_num=5R01AI040247-06&p_query=&ticket=103024486&p_audit_session_id=490423252&p_key words=>; 2 pgs.

Stephans, David, "Regulation of capsule biosynthesis in *N. meningitidis*," Grant Abstract, Grant No. 5RO1AI040247-07 [online]. National Institute of Allergy and Infectious Diseases, National Institutes of Health. Project dates Jul. 1, 1997 to Feb. 28, 2002 [retrieved on Aug. 21, 2009]. Retrieved from the Internet: <http://crisp.cit.nih.gov/crisp/CRISP_LIB.getdoc?textkey=6698811&p_grant_num=5R01AI040247-07&p_query=&ticket=103024486&p_audit_session_id=490423252&p_key words=>; 2 pgs.

Stephans, David, "Regulation of capsule biosynthesis in *N. meningitidis*," Grant Abstract, Grant No. 5RO1AI040247-08 [online]. National Institute of Allergy and Infectious Diseases, National Institutes of Health. Project dates Jul. 1, 1997 to Feb. 28, 2002 [retrieved on Aug. 21, 2009]. Retrieved from the Internet: <http://crisp.cit.nih.gov/crisp/CRISP_LIB.getdoc?textkey=6845110&p_grant_num=5R01AI040247-08&p_query=&ticket=103024486&p_audit_session_id=490423252&p_key words=>; 2 pgs.

Stephans, David, "Regulation of capsule biosynthesis in *N. meningitidis*," Grant Abstract, Grant No. 5RO1AI040247-09 [online]. National Institute of Allergy and Infectious Diseases, National Institutes of Health. Project dates Jul. 1, 1998 to Feb. 28, 2008 [retrieved on Aug. 21, 2009]. Retrieved from the Internet: <http://crisp.cit.nih.gov/crisp/CRISP_LIB.getdoc?textkey=7024530&p_grant_num=5R01AI040247-09&p_query=&ticket=103024486&p_audit_session_id=490423252&p_keywords=>; 2 pgs.

Suggs et al., "Use of synthetic oligodoexyribonucleotides for the isolation of specific cloned DNA sequences," in *ICB-UCLA Symposia on Molecular and Cellular Biology vol. XXIII, 1981: Developmental Biology Using Purified Genes*. Brown, (Ed.) Academic Press: New York, NY; 1981. Cover page, publisher's page and pp. 683-693.

Wahlen et al., "The changing epidemiology of invasive meningococcal disease in Canada, 1985 through 1992," Feb. 1, 1995 *JAMA* 273(5):383-389.

Wei et al., "Isolation and comparison of two molecular species of the BAL 31 nuclease from *Alteromonas espejiana* with distinct kinetic properties," Nov. 25, 1983 *J. Biol. Chem.* 258(22):13506-13512.

Whitfield and Roberts, "Structure, assembly, and regulation of expression of capsules in *Escherichia coli*," Mar. 1999 *Mol. Microbiol.* 31(5):1307-1319.

Wigley et al., "The serine acetyltransferase from *Escherichia coli*. Over-expression, purification, and preliminary crystallographic analysis," Dec. 17, 1990 *FEBS Lett.* 277(1-2):267-271.

World Health Organization, *Meningitis in Africa. The constant challenge of epidemics.* WHO 21:15; Mar. 1996.

*World Health Report 1996.* World Health Organization, Geneva, Switzerland.

Wu (Ed.), *Methods in Enzymology vol. 68.* Academic Press: New York, NY; 1979. Cover page, publisher's page and table of contents.

Wu et al. (Eds.), *Methods in Enzymology vol. 100*. Academic Press: New York, NY; 1983. Cover page, publisher's page and table of contents.

Wu (Ed.), *Methods in Enzymology vol. 218, part I*. Academic Press, Inc. Harcourt Brace & Company: San Diego, CA; 1993. Cover page, publisher's page and table of contents.

Yanisch-Perron et al., "Improved M13 phage cloning vectors and host strains: nucleotide sequences of the M13mp18 and pUC19 vectors," 1985 *Gene* 33(1):103-119.

* cited by examiner

```
atgttatctaatttaaaaacaggaaataatatcttaggattacctgaatttgagttgaat
ggctgccgattcttatataaaaaaggtatagaaaaaacaattattactttttcagcattt
cctcctaaagatattgctcaaaaatataattatataaaagattttttaagttctaattat
acttttttagcattcttagataccaaatatccagaagatgatgctagaggcacttattac
attactaatgagttagataatggatatttacaaaccatacattgtattattcaattatta
tcgaatacaaatcaagaagatacctacctttttgggttcaagtaaaggtggcgttggcgca
cttctactcggtcttacatataattatcctaatataattattaatgctcctcaagccaaa
ttagcagattatatcaaaacacgctcgaaaaccattctttcatatatgcttggaacctct
aaaagatttcaagatattaattacgattatatcaatgacttcttactatctaaaattaag
acttgcgactcctcacttaaatggaatattcatataacttgcggaaaagatgattcatat
catttaaatgaattagaaattctaaaaaatgaatttaatataaaagctattacgattaaa
accaaactaatttctggcgggcatgataatgaagcaattgcccactatagagaatacttt
aaaaccataatccaaaatatataa
```

FIG. 8A

```
MLSNLKTGNNILGLPEFELNGCRFLYKKGIEKTIITFSAFPPKDIAQKYNYIKDFLSSNY
TFLAFLDTKYPEDDARGTYYITNELDNGYLQTIHCIIQLLSNTQEDTYLLGSSKGGVGA
LLLGLTYNYPNIIINAPQAKLADYIKTRSKTILSYMLGTSKRFQDINYDYINDFLLSKIK
TCDSSLKWNIHITCGKDDSYHLNELEILKNEFNIKAITIKTKLISGGHDNEAIAHYREYF
KTIIQNI
```

FIG. 8B

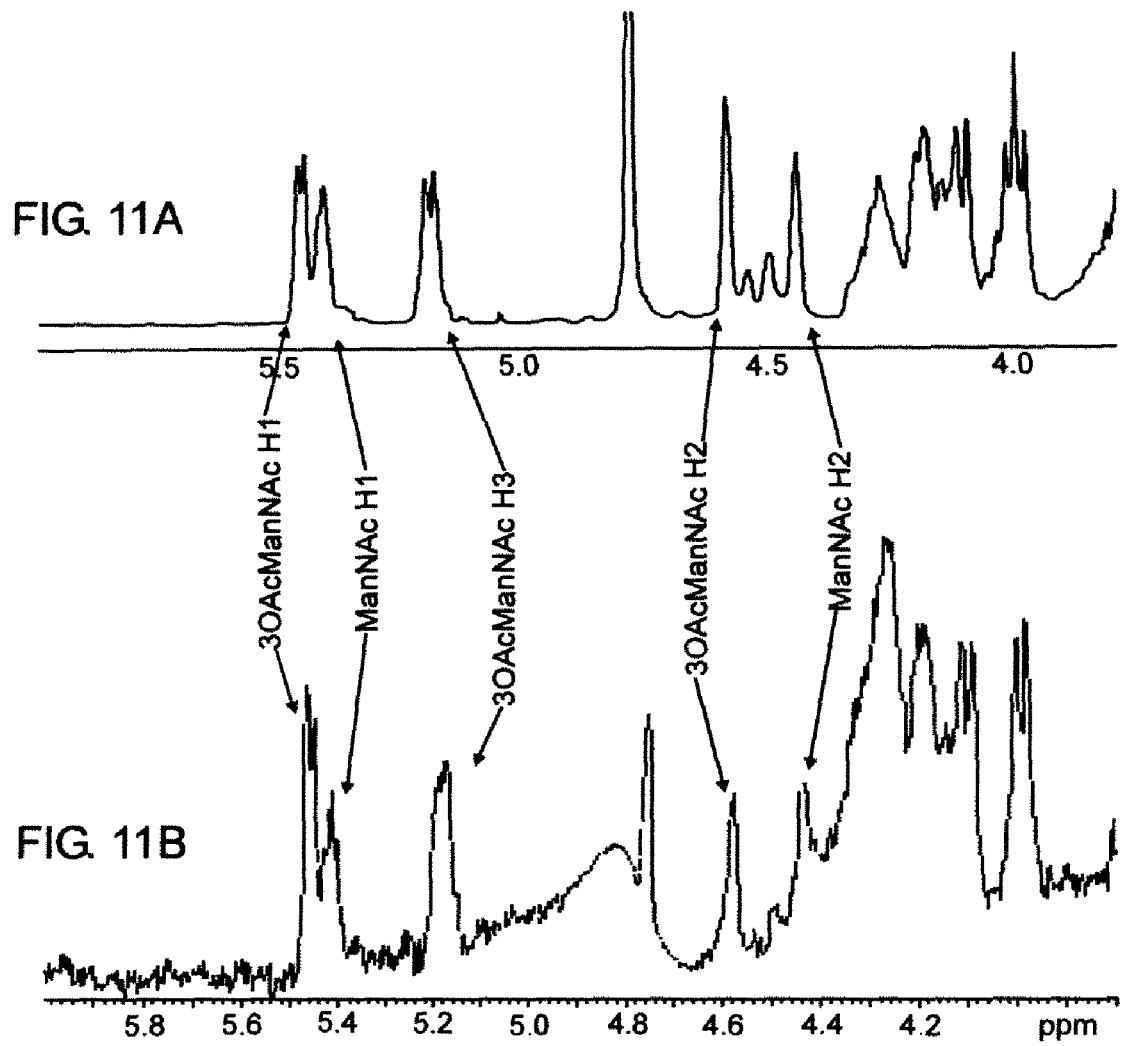

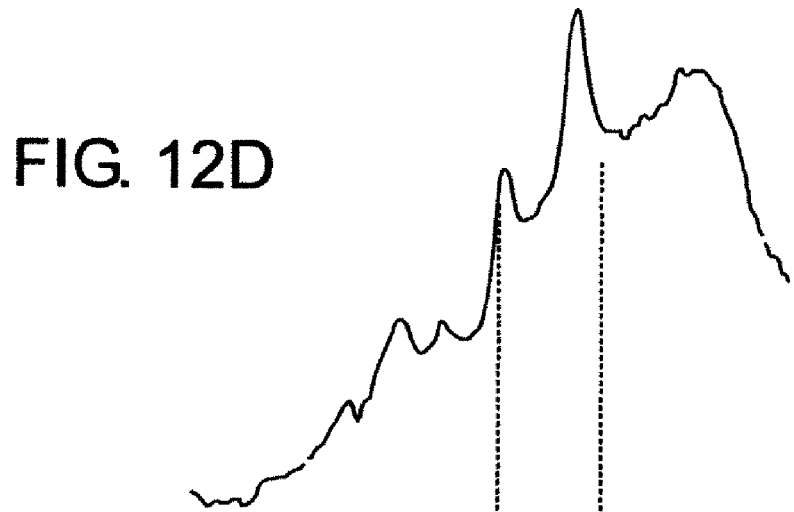
FIG. 12D
FIG. 12E
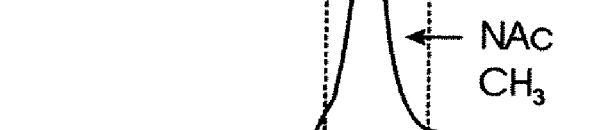
NAc CH$_3$
FIG. 12F
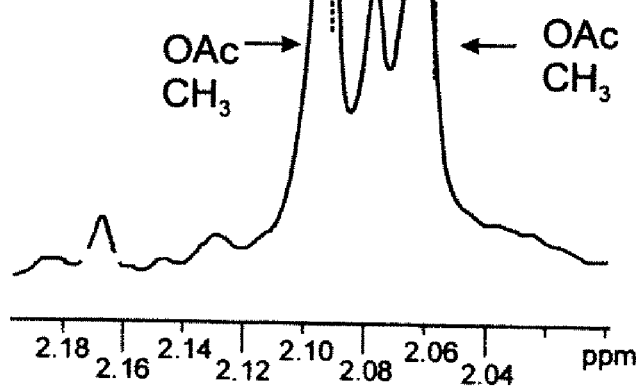
OAc CH$_3$ — OAc CH$_3$
2.18  2.16  2.14  2.12  2.10  2.08  2.06  2.04  ppm

SEQUENCE LISTING

<160> NUMBER OF SEQ ID NOS: 13

<210> SEQ ID NO 1
<211> LENGTH: 744
<212> TYPE: DNA
<213> ORGANISM: Neisseria meningitidis

<400> SEQUENCE: 1

```
atgttatcta atttaaaaac aggaaataat atcttaggat tacctgaatt tgagttgaat      60
ggctgccgat tctttatataa aaaaggtata gaaaaaacaa ttattacttt ttcagcattt     120
cctcctaaag atattgctca aaaatataat tatataaaag atttttttaag ttctaattat     180 acttttttag cattcttaga taccaaatat ccagaagatg atgctagagg cacttattac     240
```

-continued

```
attactaatg agttagataa tggatattta caaaccatac attgtattat tcaattatta      300
tcgaatacaa atcaagaaga tacctacctt ttgggttcaa gtaaaggtgg cgttggcgca      360
cttctactcg gtcttacata taattatcct aatataatta ttaatgctcc tcaagccaaa      420
ttagcagatt atatcaaaac acgctcgaaa accattcttt catatatgct tggaacctct      480
aaaagatttc aagatattaa ttacgattat atcaatgact tcttactatc taaaattaag      540
acttgcgact cctcacttaa atggaatatt catataactt gcggaaaaga tgattcatat      600
catttaaatg aattagaaat tctaaaaaat gaatttaata taaagctat tacgattaaa      660 accaaactaa tttctggcgg gcatgataat gaagcaattg cccactatag agaatacttt      720
aaaaccataa tccaaaatat ataa                                              744
```

<210> SEQ ID NO 2
<211> LENGTH: 247
<212> TYPE: PRT
<213> ORGANISM: Neisseria meningitidis

<400> SEQUENCE: 2

```
Met Leu Ser Asn Leu Lys Thr Gly Asn Asn Ile Leu Gly Leu Pro Glu
 1               5                   10                  15

Phe Glu Leu Asn Gly Cys Arg Phe Leu Tyr Lys Lys Gly Ile Glu Lys
             20                  25                  30

Thr Ile Ile Thr Phe Ser Ala Phe Pro Pro Lys Asp Ile Ala Gln Lys
         35                  40                  45

Tyr Asn Tyr Ile Lys Asp Phe Leu Ser Ser Asn Tyr Thr Phe Leu Ala
     50                  55                  60

Phe Leu Asp Thr Lys Tyr Pro Glu Asp Ala Arg Gly Thr Tyr Tyr
 65                  70                  75                  80

Ile Thr Asn Glu Leu Asp Asn Gly Tyr Leu Gln Thr Ile His Cys Ile
                 85                  90                  95

Ile Gln Leu Leu Ser Asn Thr Asn Gln Glu Asp Thr Tyr Leu Leu Gly
            100                 105                 110

Ser Ser Lys Gly Gly Val Gly Ala Leu Leu Leu Gly Leu Thr Tyr Asn
        115                 120                 125

Tyr Pro Asn Ile Ile Ile Asn Ala Pro Gln Ala Lys Leu Ala Asp Tyr
    130                 135                 140

Ile Lys Thr Arg Ser Lys Thr Ile Leu Ser Tyr Met Leu Gly Thr Ser
145                 150                 155                 160

Lys Arg Phe Gln Asp Ile Asn Tyr Asp Tyr Ile Asn Asp Phe Leu Leu
                165                 170                 175

Ser Lys Ile Lys Thr Cys Asp Ser Ser Leu Lys Trp Asn Ile His Ile
            180                 185                 190

Thr Cys Gly Lys Asp Asp Ser Tyr His Leu Asn Glu Leu Glu Ile Leu
        195                 200                 205

Lys Asn Glu Phe Asn Ile Lys Ala Ile Thr Lys Thr Lys Leu Ile
    210                 215                 220

Ser Gly Gly His Asp Asn Glu Ala Ile Ala His Tyr Arg Glu Tyr Phe
225                 230                 235                 240

Lys Thr Ile Ile Gln Asn Ile
                245
```

<210> SEQ ID NO 3
<211> LENGTH: 24
<212> TYPE: DNA

```
<213> ORGANISM: Artificial
<220> FEATURE:
<223> OTHER INFORMATION: Oligonucleotide useful as a primer

<400> SEQUENCE: 3
aatcatttca atatcttcac agcc                                              24

<210> SEQ ID NO 4
<211> LENGTH: 24
<212> TYPE: DNA
<213> ORGANISM: Artificial
<220> FEATURE:
<223> OTHER INFORMATION: Oligonucleotide useful as a primer

<400> SEQUENCE: 4
aatcatttca atatcttcac agcc                                              24

<210> SEQ ID NO 5
<211> LENGTH: 23
<212> TYPE: DNA
<213> ORGANISM: Artificial
<220> FEATURE:
<223> OTHER INFORMATION: Oligonucleotide useful as a primer

<400> SEQUENCE: 5
caaaggaagt tactgttgtc tgc                                               23

<210> SEQ ID NO 6
<211> LENGTH: 26
<212> TYPE: DNA
<213> ORGANISM: Artificial
<220> FEATURE:
<223> OTHER INFORMATION: Oligonucleotide useful as a primer

<400> SEQUENCE: 6
catcataacg gttctggcaa atattc                                            26

<210> SEQ ID NO 7
<211> LENGTH: 26
<212> TYPE: DNA
<213> ORGANISM: Artificial
<220> FEATURE:
<223> OTHER INFORMATION: Oligonucleotide useful as a primer

<400> SEQUENCE: 7
ctgtatcagg ctgaaaatct tctctc                                            26

<210> SEQ ID NO 8
<211> LENGTH: 27
<212> TYPE: DNA
<213> ORGANISM: Artificial
<220> FEATURE:
<223> OTHER INFORMATION: Oligonucleotide useful as a primer

<400> SEQUENCE: 8
gaacatatgt tatctaattt aaaaaac                                           27

<210> SEQ ID NO 9
<211> LENGTH: 30
<212> TYPE: DNA
<213> ORGANISM: Artificial
<220> FEATURE:
<223> OTHER INFORMATION: Oligonucleotide useful as a primer

<400> SEQUENCE: 9
ttactcgaga tatatatttt ggattatggt                                        30
```

```
<210> SEQ ID NO 10
<211> LENGTH: 30
<212> TYPE: DNA
<213> ORGANISM: Artificial
<220> FEATURE:
<223> OTHER INFORMATION: Oligonucleotide useful as a primer

<400> SEQUENCE: 10
ggagatatac ataagctttc taatttaaaa                                30

<210> SEQ ID NO 11
<211> LENGTH: 30
<212> TYPE: DNA
<213> ORGANISM: Artificial
<220> FEATURE:
<223> OTHER INFORMATION: Oligonucleotide useful as a primer

<400> SEQUENCE: 11
agcgaattct cagtggtggt ggtggtggtg                                30

<210> SEQ ID NO 12
<211> LENGTH: 6
<212> TYPE: PRT
<213> ORGANISM: Artificial
<220> FEATURE:
<223> OTHER INFORMATION: Partially conserved sequence motif in certain
      acetyl transferases

<400> SEQUENCE: 12

Gly Ser Ser Lys Gly Gly
1               5

<210> SEQ ID NO 13
<211> LENGTH: 5
<212> TYPE: PRT
<213> ORGANISM: Artificial
<220> FEATURE:
<223> OTHER INFORMATION: Conserved sequence motif in serine esterases

<400> SEQUENCE: 13

Gly Ser Ser Ser Gly
1               5
```

NEISSERIA MENINGITIDIS SEROGROUP A CAPSULAR POLYSACCHARIDE ACETYLTRANSFERASE, METHODS AND COMPOSITIONS

CROSS REFERENCE TO RELATED APPLICATIONS

This application is a divisional of U.S. patent application Ser. No. 11/201,774, filed Aug. 11, 2005, now abandoned which application claims benefit of U.S. Provisional Application No. 60/600,862, filed Aug. 11, 2004, both of which applications are incorporated by reference herein.

ACKNOWLEDGMENT OF FEDERAL RESEARCH SUPPORT

This invention was made, at least in part, with funding from the National Institutes of Health (Grant No. AI40247) and the Department of Energy (Grant No. DE-FG02-93ER20097). Accordingly, the United States Government has certain rights in this invention.

BACKGROUND OF THE INVENTION

The field of this invention is the area of molecular biology, in particular as related to recombinant expression of an acetyltransferase of Serogroup A *Neisseria meningitidis*, and immunogenic compositions, especially immunogenic compositions comprising fully acetylated capsule of *Neisseria meningitidis*, Serogroup A.

*Neisseria meningitidis* is a leading worldwide cause of meningitis and rapidly fatal sepsis in otherwise health individuals (Apicella, M. A. (1995) in *Principles and Practice of Infectious Diseases*, eds. Mandell, G. L., Douglas, R. G., and Bennett, J. E., Churchill Livingstone, New York, pp. 1896-1909). In excess of 350,000 cases of meningococcal disease were estimated to have occurred in 1995 (WHO Report (1996) WHO, Geneva, ISBN 92 4 1561823). The problem of meningococcal disease is emphasized by the recurrence of major epidemics due to serogroups A, B, and C *N. meningitidis* over the last 20 years, such as: the devastating serogroup A outbreak in sub-Saharan Africa in 1996 (WHO (1996) *Meningitis in Africa. The constant challenge of epidemics*. WHO 21:15 March); the recent dramatic increases in the incidence of serogroup B and C meningococcal disease in parts of North America (CDC (1995) *MMWR* 44:121-134; Jackson, L. A. et al. (1995) *JAMA* 273:390-394; Wahlen, C. M. et al. (1995) *JAMA* 273:383-389); and the emergence in Europe and elsewhere of meningococci with decreased susceptibility to antibiotics (Campos, J. et al. (1992) *J. Infect. Dis.* 166:173-177).

Differences in capsular polysaccharide chemical structure determine the meningococcal serogroups (Liu, T. Y. et al. (1971) *J. Biol. Chem.* 246:2849-58; Liu, T. Y. et al. (1971) *J. Biol. Chem.* 246:4703-12). Meningococci of serogroups B, C, Y, and W-135 express capsules composed entirely of polysialic acid or sialic acid linked to glucose or galactose (Liu, T. Y. et al. (1971) *J. Biol. Chem.* 246:4703-12; Bhattacharjee, A. K. et al. (1976) *Can. J. Biochem.* 54:1-8), while the capsule of group A *N. meningitidis* is composed of N-acetyl mannosamine-1-phosphate (Liu, T. Y. et al. (1971) *J. Biol. Chem.* 246:2849-58). The currently available capsular polysaccharide vaccines for serogroups A, C, Y, or W-135 *N. meningitidis* are effective for control of meningococcal outbreaks in older children and adults. However, because of poor immunogenicity in young children and short-lived immunity (Zollinger, W. D. and Moran, E. (1991) *Trans. R. Soc. Trop. Med. Hyg.* 85:37-43), these vaccines are not routinely used for long-term prevention of meningococcal disease.

In some epidemic settings, simultaneous or closely-linked meningococcal outbreaks have occurred in the same population due to different serogroups (Sacchi, C. T. et al. (1994) *J. Clin. Microbiol.* 32:1783-1787; CDC (1995) *MMWR* 44:121-134; Krizova, P. and Musilek, M. (1994) *Centr. Eur. J. Publ. Hlth* 3:189-194). Further, Caugant et al. (Caugant, D. A. et al. (1986) *Proc. Natl. Acad. Sci. USA* 83:4927-4931; Caugant, D. A. et al. (1987) *J. Bacteriol.* 169:2781-2792) and others have noted that meningococcal isolates of different serogroups may be members of the same enzyme type (ET)-5, ET-37 or ET-4 clonal complexes.

*Neisseria meningitidis* serogroup A is responsible for the massive epidemics of meningococcal meningitis and septicemia that periodically affect sub-Saharan Africa, China, South America and other parts of the world. The serogroup A capsular polysaccharide (CPS) that confers serogroup specificity is composed of repeating units of ($\alpha 1 \rightarrow 6$) linked N-acetyl-D-mannosamine-1-phosphate that is O-acetylated (1). Although there is evidence of other glycosidic linkages (2), the principal linkage between monomer ManNAc residues in this polysaccharide is the ($\alpha 1 \rightarrow 6$) phosphodiester bond involving the hemiacetal group of carbon 1 and the alcohol group of carbon 6 of the mannosamine residues. Serogroup A CPS is structurally distinct from other disease-causing meningococcal serogroups B, C, Y and W-135 which are composed of, or contain sialic acid (1, 3, 4).

There is a long felt need in the art for improved immunogenic compositions useful for generating a protective immune response to *Neisseria meningitidis*, which is highly contagious and causes serious illness.

SUMMARY OF THE INVENTION

The present invention provides recombinant DNA molecules which do not occur in nature, recombinant host cells and methods of using the foregoing to recombinantly produce an O-acetyltransferase derived from *Neisseria meningitidis*. This acetyltransferase transfers acetyl moieties to capsular polysaccharides, especially those of Serogroup A *N. meningitidis*. The acetyltransferase of the present invention can be purified using specific antibody in an immunoaffinity column, for example, or an affinity tag can be engineered into the recombinant protein by the use of appropriate tag (especially a polyhistidine or His tag) coding sequences fused in frame. Other oligopeptide "tags" which can be fused to a protein of interest by such techniques include, without limitation, strep-tag (Sigma-Genosys, The Woodlands, Tex.) which directs binding to streptavidin or its derivative streptactin (Sigma-Genosys); a glutathione-S-transferase gene fusion system which directs binding to glutathione coupled to a solid support (Amersham Pharmacia Biotech, Uppsala, Sweden); a calmodulin-binding peptide fusion system which allows purification using a calmodulin resin (Stratagene, La Jolla, Calif.); a maltose binding protein fusion system allowing binding to an amylose resin (New England Biolabs, Beverly, Mass.); and an oligo-histidine fusion peptide system which allows purification using a $Ni^{2+}$-NTA column (Qiagen, Valencia, Calif.).

The present invention further encompasses the acetylation (in vitro) of Serogroup A capsular polysaccharides isolated from *N. meningitidis* using acetyltransferase recombinantly produced using the recombinant host cells of the present invention.

The present invention also provides for improved immunogenic compositions comprising capsular polysaccharides of N. meningitidis, where the improvement comprises more complete acetylation of the capsular polysaccharides than is currently possible in the absence of the enzymatic acetylation by using the acetyltransferase of the present invention, especially those from Serogroup A N. meningitidis, with the result that a stronger immune response results. The immunogenic compositions of the present invention can comprise a pharmaceutically acceptable carrier and optionally can further comprise at least one immunological adjuvant or cytokine. These immunogenic compositions are useful as vaccines and as vaccine components. Desirably, the CPS is 90-95% acetylated for eliciting a robust immune response

DESCRIPTION OF THE DRAWINGS

FIG. 1 shows the genetic organization and location of the *Neisseria meningitidis* serogroup A capsule biosynthetic locus mynA-mynD (sacA-sacD), and the sites of polar (∇) and nonpolar (◇) mutations in these genes. ctrA is the first gene of the capsule transport operon and galE encodes the UDP-glucose-4-epimerase.

FIG. 2A-2C provide $^1$H NMR spectra of capsular polysaccharides (CPSs) purified from the wild type serogroup A meningococcal strain F8229 (FIG. 2A) the mynC::aphA-3 mutant (FIG. 2B) and the mynC::aphA-3 mutant complemented with (mynC), with IPTG induction (FIG. 2C). Insets are the enlargements of the N/O—Ac methyl proton regions.

FIG. 3 demonstrates over-expression and purification of MynC of serogroup A *N. meningitidis*. Lane 1, molecular weight marker; 2, cell lysate before IPTG induction; 3, cell lysate after IPTG induction; 4, cell lysate on the nickel-nitrilotriacetic acid (Ni-NTA) column 5, flow through of the Ni-NTA column; 6, wash 1; 7, wash 2; 8, wash 3; 9, elution using 250 mM imidazole containing buffer. Arrow indicates the ~26 kDa His tagged MynC protein.

FIG. 4 is an autoradiogram showing the in vitro O-acetyltransferase activity of MynC. $^{14}$C-labeled acetyl coenzyme A and meningococcal CPSs were the substrates. Lanes (1) sample buffer alone, lanes 2-4 reactions from various acceptor polymers plus 5 μg MynC (2) serogroup B CPS, (3) serogroup C CPS, (4) CPS of the serogroup A wild type strain F8229, (5) and (6) partially purified CPS of F8229/mynC::aphA-3 mutant at 5 and 10 μg MynC respectively, (7) and (8) SEPHACRYL 200 gel filtration column purified CPS of F8229/mynC::aphA-3 mutant with 5 and 10 μg MynC respectively, (9) column purified CPS of F8229/mynC::aphA-3 mutant with proteins eluted from a lysate of the *E. coli* strain carrying the pET20b vector without insert, and (10) column purified CPS of the F8229/mynC::aphA-3 mutant alone. Each reaction was performed with 50 μg of CPS and 10 μg of MynC, and analyzed as described in experimental procedures.

FIGS. 5A-5C characterize O-acetyltransferase activity of purified MynC as measured by $^{14}$C incorporation. FIG. 5A demonstrates concentration-dependent incorporation of the $^{14}$C-labeled acetyl moiety by MynC into the mynC::aphA-3 CPS. FIG. 5B shows time kinetics of the incorporation of the $^{14}$C-labeled acetyl moiety into the mynC::aphA-3 CPS by MynC. FIG. 5C shows the pH optima of MynC activity in citrate (4.5 to 6.5), phosphate (5.8 to 8) and borate (8.5 to 10.5) buffers.

FIG. 6A shows whole cell ELISA with mAb 14-1-A. 1, wild type parent F8229; 2, unencapsulated strain F8239; 3, mynC::aphA-3 nonpolar mutant; 4, mynC::aphA-3 nonpolar mutant complemented with pGS205 (mynC) in the absence of IPTG induction; and 5 mynC::aphA-3 nonpolar mutant complemented with pGS205 (mynC) in the presence of IPTG induction. FIG. 6B illustrates Western blot analysis with whole cell lysates demonstrating the His-tagged MynC in the presence (+) or absence (−) of IPTG. Lanes 1, M.W. marker (32.3 KDa); 2, wild type strain F8229; 3 and 4, overexpressed wild type strain NmAwtc1; 5 and 6, complemented nonpolar mutant NmAnpc1.

FIG. 7A shows the cellular localization of MynC. Western blot analysis of sub-cellular fractions of mynC complemented strain NmAnpc1 using $(His)_5$ mAb. The loadings of individual fractions were standardized based on a set amount of cells obtained from 500 ml culture. FIG. 7B demonstrates peripheral and strong membrane association of MynC. Total membrane obtained from NmAnpc1 cells was extracted with buffer alone, 1M NaCl, 6M urea or buffer with 1% TX-100 as described in the Materials and Methods. After centrifugation, soluble fraction (S) were concentrated by precipitation with trichloroacetic acid, pellets (P) were resuspended directly in sample buffer. Fractions were subjected to 10% SDS-PAGE gels and analyzed by western blots using $(His)_5$-specific mAb.

FIGS. 8A and 8B show the coding and amino acid sequences for the *N. meningitidis* mynC, respectively. See also SEQ ID NO:1 and SEQ ID NO:2, respectively.

FIG. 9 shows the results of a normal human serum (10% v/v) bactericidal activity assay with the OAc+/CAP+ *N. meningitidis* wild-type parent F8229 (lane 1), the serogroup A CAP− strain F8239 (lane 2), the CAP− mutants of strain F8229 (mynA, lane 3; mynB, lane 4) and the OAc−/CAP+ mynC::aphA3 (lane 5) mutant of F8229. Percentage of meningococcal survival in the presence of normal human serum (black bars) and in the presence of heat inactivated (56° C., 30 min) serum (gray bars) is shown.

FIGS. 10A and 10B show the results of competitive inhibition ELISAs performed using purified CPS of the serogroup A *N. meningitidis* OAc+/CAP+ wild-type parent F8229 (FIG. 11A) and the OAc−/CAP+ mynC::aphA3 mutant (FIG. 11B), and sera obtained from six different individuals (numbered in side legend) previously vaccinated with a licensed vaccine containing the serogroup A polysaccharide.

FIGS. 11A-11B provide a comparison of $^1$H NMR spectra of the anomeric and the ring proton regions of serogroup A *N. meningitidis* wild type parent strain F8229 using the isolated CPS at 500 MHz (FIG. 11A) and whole cells by HR-MAS at 600 MHz (FIG. 11B).

FIGS. 12A-12C provide comparisons of whole cell HR-MAS $^1$H NMR patterns in the anomeric and ring proton regions of serogroup A *N. meningitidis* wild type parent F8229 (FIG. 12A), capsule O-acetylation negative mutant strain NMA001 (FIG. 12B) and capsule negative serogroup A strain F8239 (FIG. 12C). FIG. 12D-12F provide a comparison of whole cell HR-MAS $^1$H NMR patterns in the O—Ac, N—Ac methyl proton region of serogroup A *N. meningitidis* wild type parent F8229 (FIG. 12D), capsule O-acetylation negative mutant strain NMA001 (FIG. 12E) and capsule negative serogroup A strain F8239 (FIG. 12F).

DETAILED DESCRIPTION OF THE INVENTION

The abbreviations used herein are CPS, capsular polysaccharide; O—Ac CPS, O-acetylated capsular polysaccharide; PCR, polymerase chain reaction; GC-MS, gas-liquid chromatography-mass spectrometry; COSY, $^1$H-$^1$H correlation spectroscopy; TOCSY, total correlation spectroscopy; High Resolution Magic Angle Spinning NMR Spectroscopy, HR-MAS NMR; mAb, monoclonal antibody; ELISA: enzyme linked immunosorbant assay; SDS-PAGE, sodium dodecyl sulfate-polyacrylamide gel electrophoresis; DOC-PAGE, deoxycholate-polyacrylamide gel electrophoresis; ManNAc, N-acetyl mannosamine.

Capsular polysaccharide is the critical virulence determinant in N. meningitidis and Four (A, C, Y, and W-135) of the five clinically important meningococcal disease causing serogroups express O-acetylated capsules (1, 3, 30, 31). We describe herein the identification of the serogroup A CPS biosynthetic gene mynC and its gene product MynC. MynC is required for serogroup A meningococcal capsular O-acetylation; it is the O-3 and O-4 N-acetyl mannosamine acetyltransferase. MynC represents a new class of O-acetyltransferase with no homology with known O-acetyltransferases or the proposed sialic acid capsular serogroup C, Y, and W-135 meningococcal O-acetyltransferases OatC or OatWY reported recently (5). MynC is an inner membrane-associated protein with no transmembrane domains. It seems to be a peripheral protein having tight association with the inner membrane and could be disrupted only by stringent 6 M urea wash and not by a more mild 1 M NaCl wash. The inability of TX-100 condition to extract the MynC off the membrane, confirms that this protein is not an integral membrane protein as also indicated by transmembrane domain search. The strong association of MynC with the membrane suggests that this protein could be a component of multi-protein complex engaged in capsule biosynthesis.

O-acetylation of bacterial surface polysaccharides such as capsular polysaccharides, exopolysaccharides, peptidoglycans and lipooligosaccharides is common in pathogens and in symbionts, O-acetylation has immunogenic and functional importance. N. meningitidis, K1 E. coli, S. pneumoniae, Salmonella enterica, Staphylococcus aureus and Pseudomonas aeruginosa can express O-acetylated CPS (31,32). In S. enterica serovar typhi (7) and in E. coli K1 (6), the loss of O-acetylation from CPS results in loss of immunogenicity, whereas for meningococcal serogroup C (30) and pneumococcal type 9V (33) capsules, O-acetylation is not required for the induction of protective antibodies. In the extracellular polysaccharide alginate polymer, produced by isolates of P. aeruginosa from patients with cystic fibrosis, D-mannuronic acid is O-acetylated at O-2 and at O-3 by three genes algI, algJ, and algF (34). Alginate O-acetylation had been shown to contribute to biofilm architecture, microcolony formation (35) and resistance to opsonic phagocytosis (36). O-acetylation is also important for rhizobium-legume symbiosis. The rhizobial Nod factors may be O-acetylated at distinct sites to define the host specificity and the formation of the pre-infection thread and the root nodule (37-39). In Proteus mirabilis, N. gonorrhoeae and N. meningitidis (40), C-6 hydroxyl of N-acetyl muramyl residues in peptidoglycans are O-acetylated to confer both intrinsic and complete resistance to lysozyme hydrolysis. These peptidoglycan motifs are pathogen-associated molecular patterns recognized by the innate immune system (41,42).

A number of acetyltransferases that transfer an acetyl group from acetyl-CoA to O-acetylate dissimilar substrates have been identified in prokaryotic and eukaryotic systems but these proteins share limited sequence homology. Two families of proteins that O-acetylate exported carbohydrate moieties have been reported. The NodL-LacA-CysE family (43-47) that include the lipochitin acetyltransferase (NodL) of Rhizobium leguminosarum, galactoside acetyltransferases (GAT) such as LacA, the cysteine biosynthetic enzyme (CysE), also known as the serine acetyltransferase of E. coli, are cytoplasmic proteins that use acetyl coenzyme A as the acetyl donor. Interestingly, the proposed sialic acid O-acetyltransferases of meningococcal serogroups W-135 and Y (OatWY) but not of serogroup C (OatC) show sequence homology to the NodL-LacA-CysE family. The second family comprises integral membrane proteins. Members of this family include the O-acetyltransferases that O-acetylate macrolide antibiotics (Streptomyces spp.) (48), LPS O-antigen (Legionella pneumophila Lag-1, (49) Salmonella typhimurium OafA (50), Shigella flexneri bacteriophage SF6 OAc (51) and Nod factors (Rhizobium leguminosarum NodX (52). However, the putative capsule O-acetyltransferases (50) of Streptococcus pneumoniae serotype 9V, Cps9vM and Cps9vO the S. aureus serotype 5 O-acetyltransferase (53) and alginate O-acetylation proteins AlgI, AlgJ and AlgF of P. aeruginosa share no homology with the above mentioned families of O-acetyltransferases. Similarly, MynC represents a novel subclass of acetyltransferases.

The enzymatic activity for capsular polysialic acid O-acetylation from K1 E. coli was reported by Higa and Varki (54), but the respective gene and the protein have not been identified. MynC does show sequence homology with several proteins (Table 2), including the acetyl esterase (acetyl xylosidase) that degrades xylan from the thermophile, Caldicellulosiruptor saccharolyticus. These proteins share with MynC a semi-conserved motif GSSKGG (SEQ ID NO:12) in the N-terminal region. Typically, serine esterases contain a conserved GSSSG (SEQ ID NO:13) motif (assumed to be the catalytic N-terminal domain), where the middle S residue is the active site nucleophile (55). MynC also has homology (25% identity and 46% homology) with capsule biosynthesis enzyme Cap8I (464 aa) of S. aureus subsp. aureus MW2 (27) and to a hypothetical esterase/lipase/thioesterase family protein (265 aa) of Arabidopsis thaliana. The S. aureus serotype 8 capsule has O-acetylation in the mannuronic acid component of the capsule.

A BLAST search performed with the deduced MynC (247 aa) amino acid sequence (SEQ ID NO:2), identified five proteins in the Gen Bank with 25% sequence identity (Table 2). Among these were EpsK of Lactococcus lactis subsp. cremoris, acetyl esterase/xylosidase (EC 3.1.1.6, 266 aa) XynC of Caldicellulosiruptor saccharolyticus (26), and a capsular polysaccharide synthesis protein, Cap8I (464 aa), from Staphylococcus aureus subsp. aureus MW2 (27). Interestingly, these five proteins shared with MynC a semi-conserved motif (GSSKGG) SEQ ID NO:12 of mostly hydrophobic small amino acids in the N-terminal region. Repeated search and pairwise comparison of known O-acetyltransferases from prokaryotes and eukaryotes revealed no significant homology with MynC.

A motif scan search of the MynC sequence at ISREC (Swiss Institute for Experimental Cancer Research) and SIB (Swiss Institute for Bioinformatics) sites revealed no matches. Search results using the SIB-PROSITE database of protein families and domains showed no similarity. Using a Markov model for transmembrane domain prediction, TMHMM (Centre for Biological Sequence Analysis, Technical University of Denmark, Lyngby, Denmark) MynC has no transmembrane domains. EMBL-EBI (European Bioinformatics Institute) InterProScan predicted MynC as a member of alpha/beta-hydrolases super-family that includes acetylcholinesterases, carboxylesterases, mycobacterial antigens, and acetylesterases.

Growth of the mynC nonpolar mutant was not different in GC medium when compared with the wild type parent. However, when the pellets from one liter cultures of similar growth ($OD_{600}$ of 1.0) were compared for CPS yields, the mynC mutant consistently yielded 25-30% less CPS compared to the wild type parent, probably due to some polarity of the insertion mutant or due to a decrease of transcript stability. Capsular polysaccharides from the wild type strain F8229 and the nonpolar mynC mutant NMA001 were prepared, purified and subjected to compositional and structural analysis. The GC-MS analysis of the alditol acetate derivatives, after removal of the phosphate groups by HF treatment, revealed ManNAc as the sole component of capsular polysaccharides isolated from both the wild type strains and the mynC mutant.

In order to investigate the extent of O-acetylation and the location of the O-acetyl groups, the CPSs were subjected to 1-D and 2-D $^1$H NMR spectroscopic analyses. Assignments of the various protons could be made from the COSY and TOCSY NMR analyses. The wild type CPS 3-O—Ac proton assignments (Table 3) were compared to published values (28,29) and were highly consistent with these values. However, the mynC mutant CPS spectrum was quite distinct.

Figure 2A:
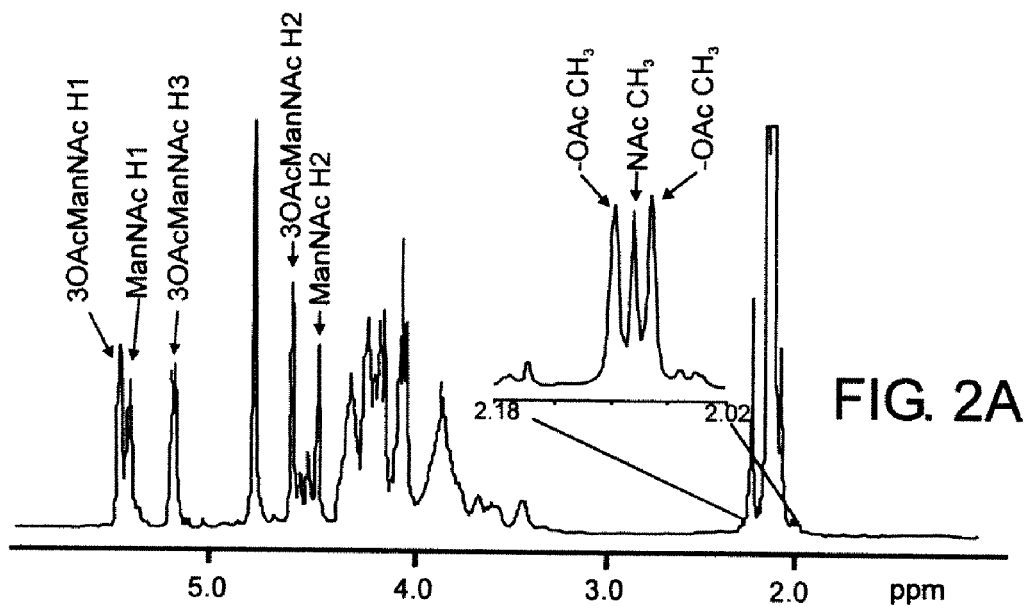
Figure 2B:
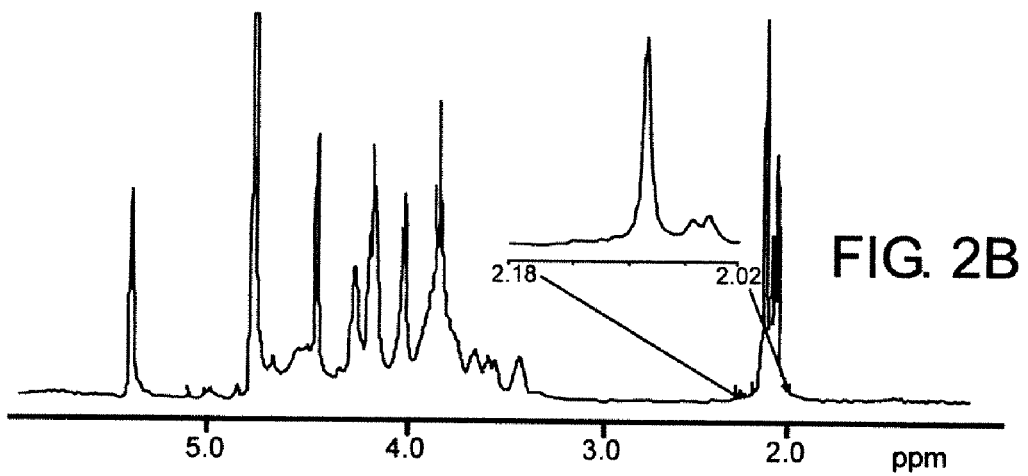
Figure 2C:
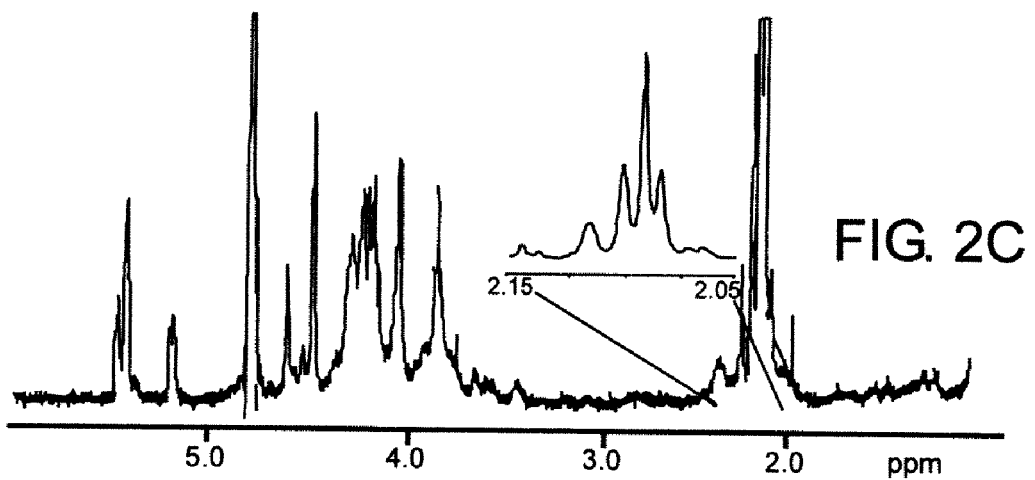

In the wild type CPS $^1$H NMR spectrum shown in FIG. 2A, the H-3 proton of ManNAc was observed at 5.20 ppm when the moiety had acetylation at O-3 due to the de-shielding effect of the acetyl group. The absence of this peak in the spectrum of the mutant CPS (FIG. 2B) indicated the lack of acetylation at O-3 on the ManNAc residue. The H-2 resonance at 4.61 ppm was observed in the wild type CPS indicating 3-0 acetylation, whereas in the mynC mutant spectrum this peak was missing (comparing FIGS. 2A-2B). In the region between 2.05 to 2.10 ppm where N- and O acetyl methyl protons were observed (inset, FIG. 2A, and Table 3) three peaks were identified in the wild type CPS spectrum. Two of these peaks corresponded to O-acetyl methyl protons, while the other was due to N-acetyl methyl protons. However, in the spectra (inset, FIG. 2B and Table 3) of the mynC mutant CPS only one peak corresponding to the N-acetyl methyl proton resonance at 2.08 ppm was observed, suggesting the absence of O-acetylation. These differences in 1-D NMR spectra indicated the absence of O-acetylation in the mynC mutant CPS.

The relative percentages of the CPS populations (Table 4) from the wild type parent and mynC mutant were calculated using integration values of the H2 resonance (28,29). Integration of the ManNAc H2 resonances for the various CPSs revealed that wild type CPS consisted of 3-O—Ac (4.59 ppm), 4-O—Ac (4.54 ppm when adjacent to 3-O—Ac-ManNAc and 4.50 ppm when adjacent to non-O-acetylated ManNAc) and Non-O—Ac (4.45 ppm) forms in the ratio of 4:2.7:3:3, and this value was found to be consistent among different batch preparations. CPS of the mynC mutant showed a 100% non-O—Ac form (peak at 4.45 ppm). In conclusion, absence of both 3 and 4 O-acetylation in mutant CPS suggested that MynC was responsible for the O-acetylation at both positions.

To further confirm the NMR data, a colorimetric estimation (25) of O-acetylation of triplicate samples of 400 and 1000 µg amounts of purified CPS from the wild type parent and mynC mutant was performed. The wild type CPS showed significant O-acetylation (at 500 nm OD±S.D of 0.2138±0.015 and 0.4896±0.003, respectively) whereas the CPS of the mynC mutant yielded minimal absorbance (at 500 nm OD±S.D of 0.0553±0.014 and 0.1400±0.028 respectively) likely due to N-acetylation.

In further studies of Serogroup A capsular polysaccharides, N. meningitidis cells were grown, and HR-MAS NMR analysis was performed following the methods described previously (68). Briefly, bacteria grown overnight on GC-agar plates (~10$^{10}$ cells) were harvested and killed in 1 ml of 10 mM potassium-phosphate buffer (pH 7.4) in D$_2$O containing 10% sodium azide (w/v). The suspension was incubated for 1 h at room temperature. The bacteria were pelleted by centrifugation (9700×g for 2 min) and washed once with 10 mM potassium phosphate buffer in D$_2$O. The pellet was mixed with 20 µl of D$_2$O containing 0.75% (w/v) TSP (3-(trimethylsilyl)-propionic acid-D$_4$, sodium salt) as an internal standard (0 ppm) prior to being loaded into a 40 µL nano NMR probe (Varian, Palo Alto, USA). HR-MAS experiments were performed using a Varian Inova 600-MHz spectrometer. Spectra were spun at 3 kHz and recorded at ambient temperature (21° C.). The experiments were performed with suppression of the HOD signal at 4.8 ppm by presaturation. Proton spectra of bacterial cells were acquired with the Carr-Purcell-Meiboom-Gill (CPMG) pulse sequence (90-(τ-180-τ)$_n$-acquisition) to remove broad lines arising from lipids and solid-like-material. The total duration of the CPMG pulse (n*2τ) was 10 ms with τ set to (1/MAS spin rate). Typically spectra were acquired each with 400 acquisitions in approximately 15 min. with a recycle delay of 2.5 sec.

Figure 12A:
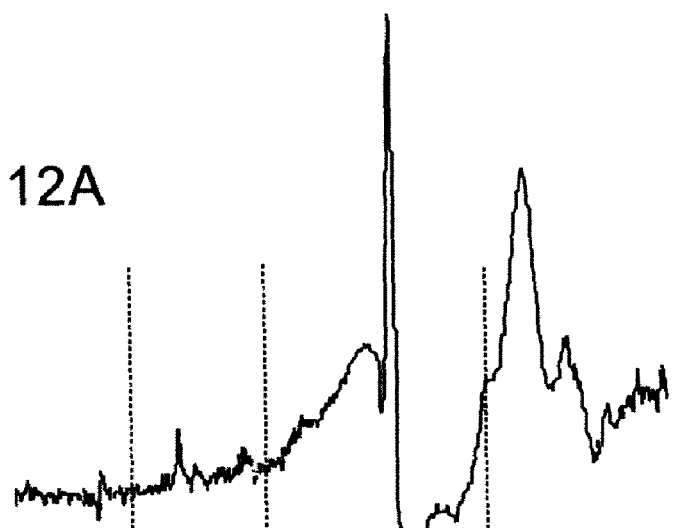
Figure 12B:
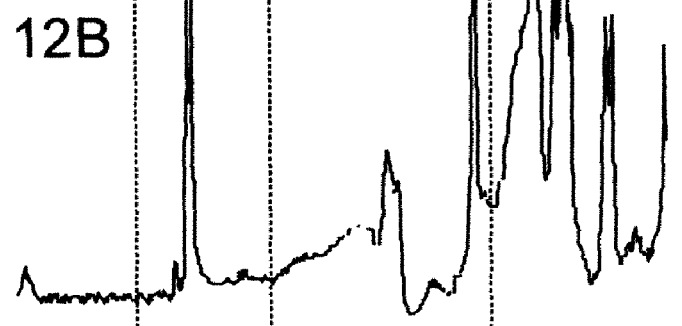
Figure 12C:
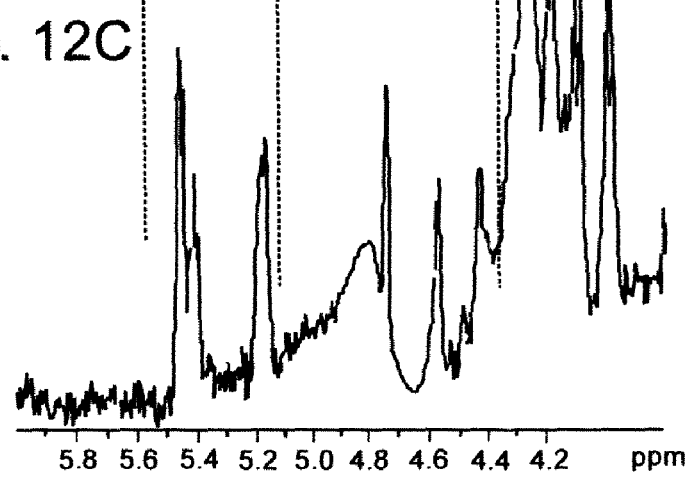

Purified meningococcal CPSs have been extensively investigated using $^1$H and $^{13}$C NMR spectroscopy (3, 61, 28) and O-acetylation patterns of CPSs have been validated using NMR techniques (29) for meningococcal polysaccharide containing vaccines. We have described purified serogroup A CPS by $^1$H NMR to identify the serogroup A O-acetyltransferase encoding gene mynC. When the O-3, O-4, OAc+ serogroup A wild type F8229 meningococci were subjected to HR-MAS analysis (FIG. 12A), reproducible serogroup A CPS derived proton resonances were noted. The respective CPS derived HR-MAS proton signals were easily correlated with the $^1$H NMR signals obtained from purified CPS (FIG. 12B) with identical chemical shifts. The characteristic anomeric peaks corresponding to 3-O-acetyl ManNAc H1 and ManNAc H1 were observed at 5.46 and 5.44 ppm, respectively and the 3-O-acetyl ManNAc H2 and ManNAc H2 observed at 4.61 ppm and 4.4 ppm, respectively. Wild type 3-O-acetylated ManNAc H3 signal was observed at 5.20 ppm and O-acetyl methyl protons were observed at 2.10 and at 2.06 ppm (see FIGS. 12D-12F). To further validate these data, the wild type stain, a capsule O-acetylation deficient mutant of this strain and a capsule defective stain were studied by HR-MAS (FIG. 12A-12C). When compared to the wild type parent (FIG. 12A), the mynC mutant meningococci gave a profile (FIG. 12B) lacking the peaks at 5.20 ppm, 4.59 ppm, 2.10 ppm and 2.06 ppm typical of a non-O-acetylated serogroup A CPS. A comparison of an enlarged high field region, 2-2.18 ppm (FIG. 12D-12F), confirmed the lack of OAc methyl proton signals in the mynC mutant spectrum (FIG. 12B) that showed a single N-acetyl methyl proton resonance at 2.08 ppm. The capsule-negative strain F8239 showed no resonance characteristic of CPS indicating the lack of capsule on the surface (e.g., FIGS. 12C and 12F).

The degree of 3-O acetylation was estimated from peak integrals obtained using the standard Varian software. The relative amount of the 3-O—Ac form of the CPS was calculated from integrals of the H-1 resonances at 5.46 ppm (3-O—Ac ManNAc) and 5.41 ppm (ManNAc) and found to be 1.6:1 (i.e. 57+/−3%). Additionally, comparison of the 3-O—Ac ManNAc H-3 integral with that of the combined anomeric region gave 50+/−3% of the 3-O—Ac form. These results agree well with the 50% 3-0 acetylation described herein. See also Gudlavalleti et al. (69). The H-2 resonance of the ManNAc residue was shown previously (28) to be sensitive to not only 3-0 acetylation but also to acetylation at O-4 in the purified capsular polysaccharide. Peaks at 4.59 ppm, 4.54 ppm and 4.50 ppm in the HR-MAS spectrum of whole cells are consistent with those reported for purified CPS H2 of 3-O-acetylated ManNAc, 4-O—Ac-ManNAc adjacent to a 3-O-acetylated ManNAc residue, and 4-O—Ac-ManNAc adjacent to a non-acetylated ManNAc residue, respectively. Although the peak integration was less precise, the degree of 4-O-acetylation was estimated to be half of the level of 3-O acetylation (i.e., approximately 25% of the CPS). This result is in agreement with the level of 27% acetylation at the 4-O position of ManNAc in purified serogroup A CPS determined in an independent experiment. These studies indicate that HR-MAS NMR technique can be applied to directly determine and quantitate the structures of CPS that are surface expressed.

Figure 3:
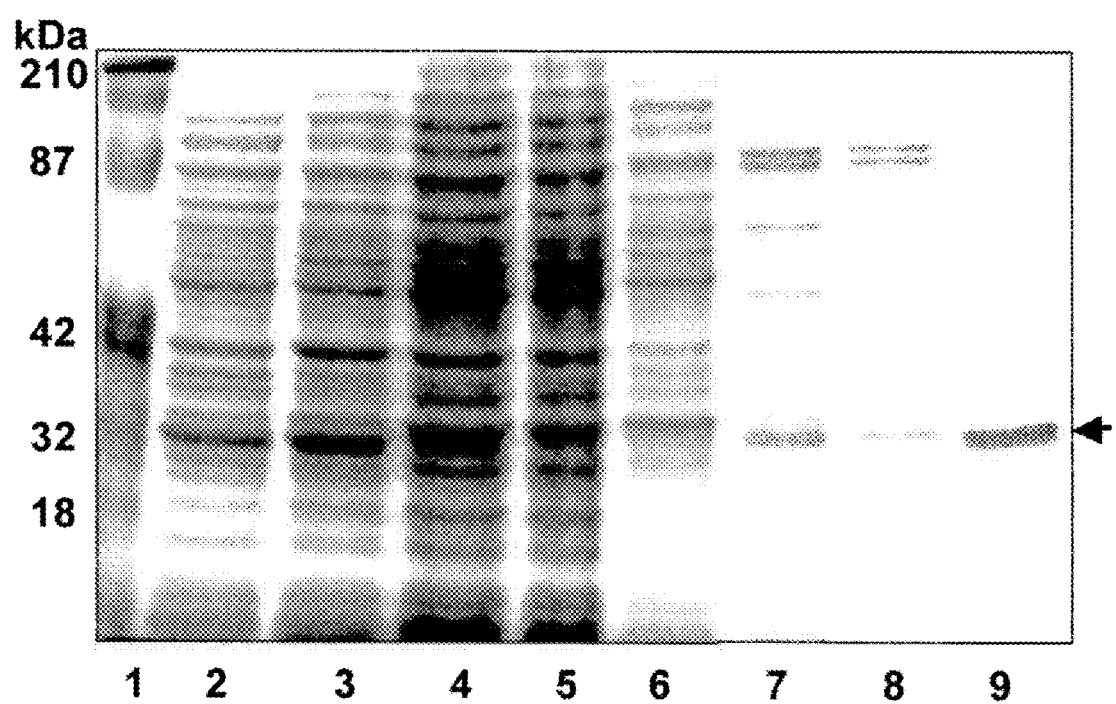

To confirm the acetyltransferase activity in an in vitro assay, MynC was His-tagged at its C-terminus, over-expressed in E. coli and purified in native conditions using Ni-NTA affinity chromatography (FIG. 3). The column was washed with buffer containing 10, 20 and 40 mM imidazole respectively. A 40 mM imidazole wash was required to remove high molecular weight contaminating bands (lane 8, FIG. 3). Elution of MynC with 250 mM imidazole containing buffer yielded a purified protein (lane 9, FIG. 3).

Figure 4:
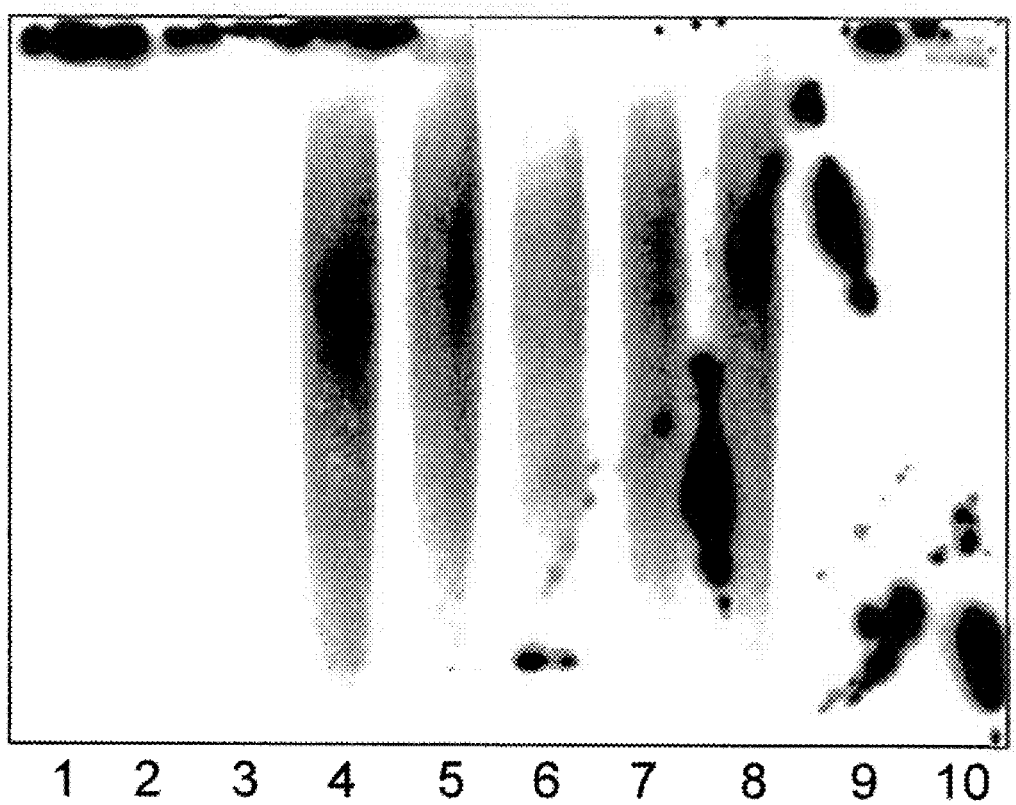
Figure 5A:
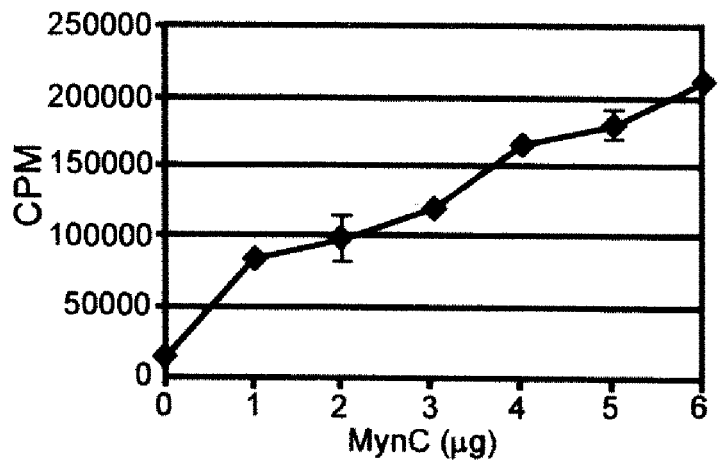
Figure 5B:
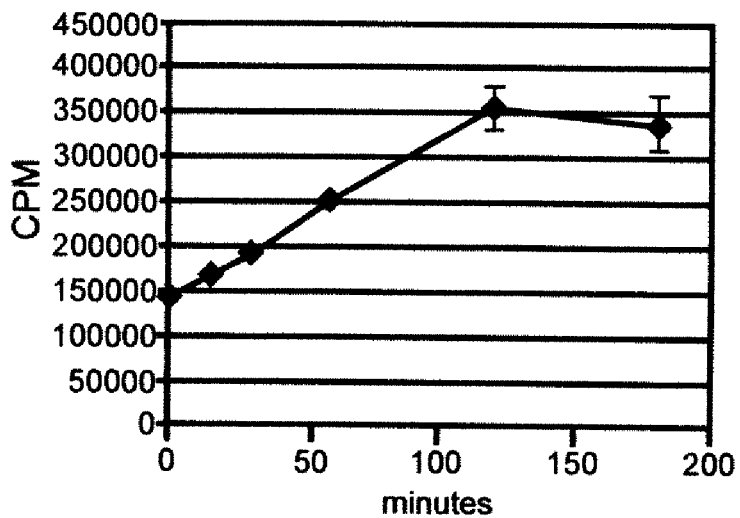
Figure 5C:
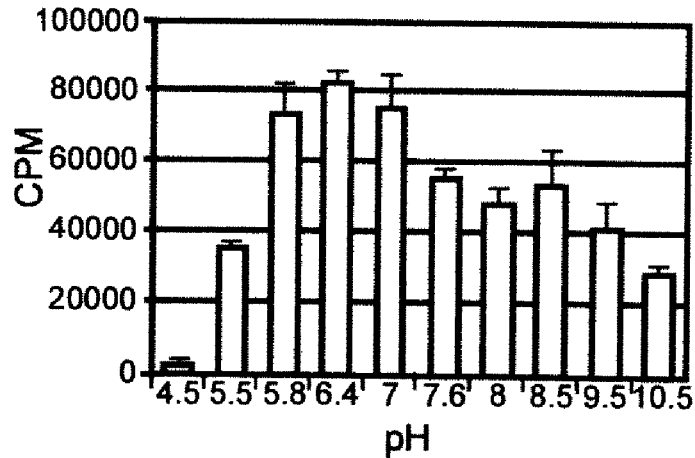
Figure 6A:
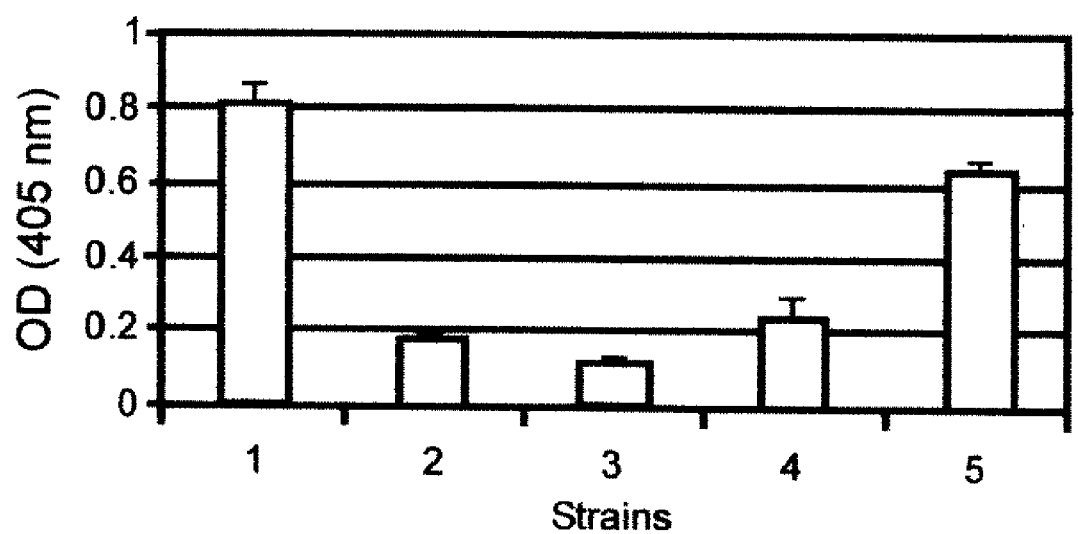
Figure 6B:
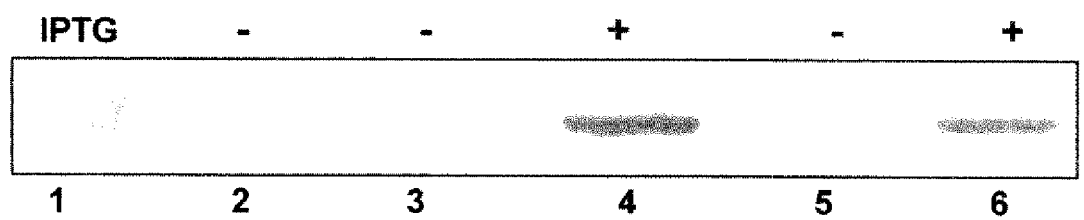
Figure 7A:
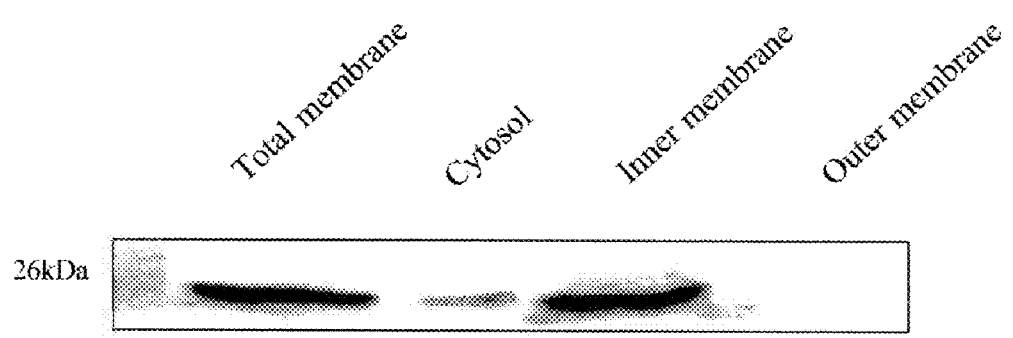
Figure 7B:
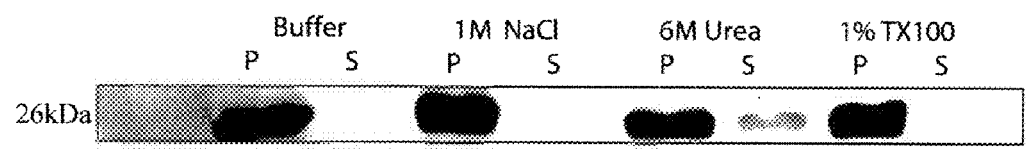
Figure 9:
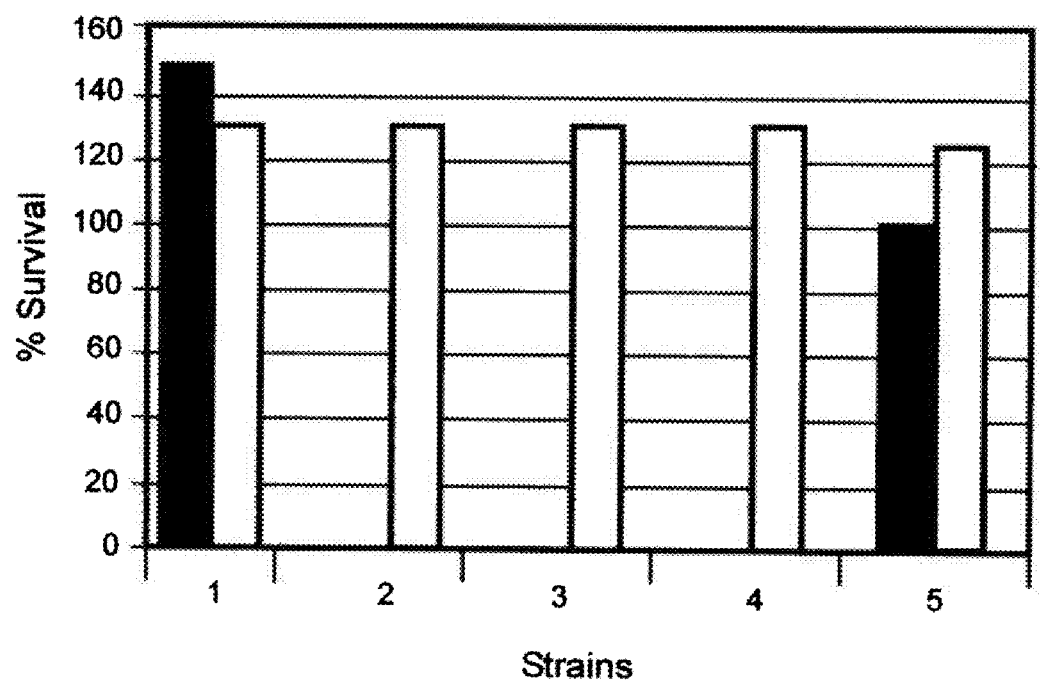
Figure 10A:
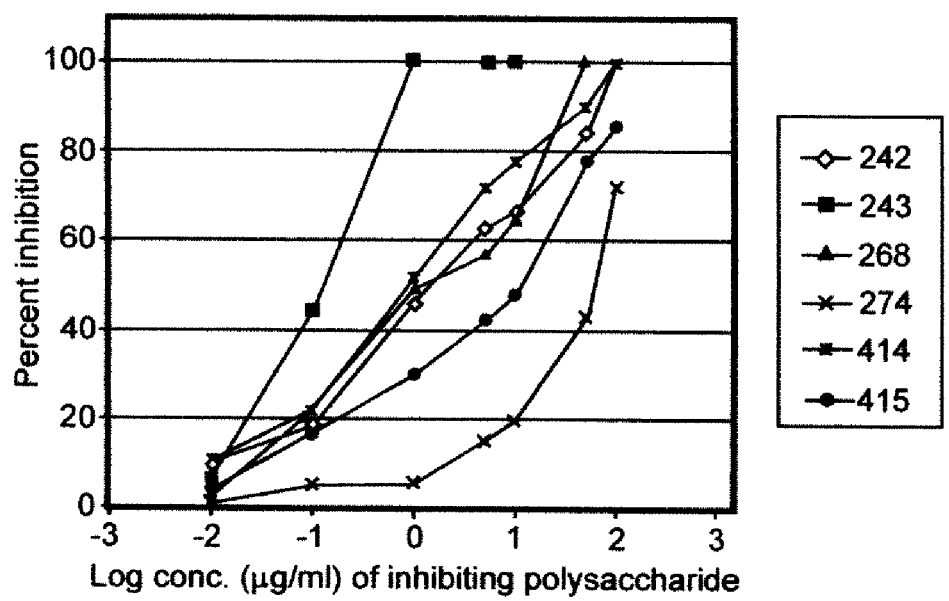
Figure 10B:
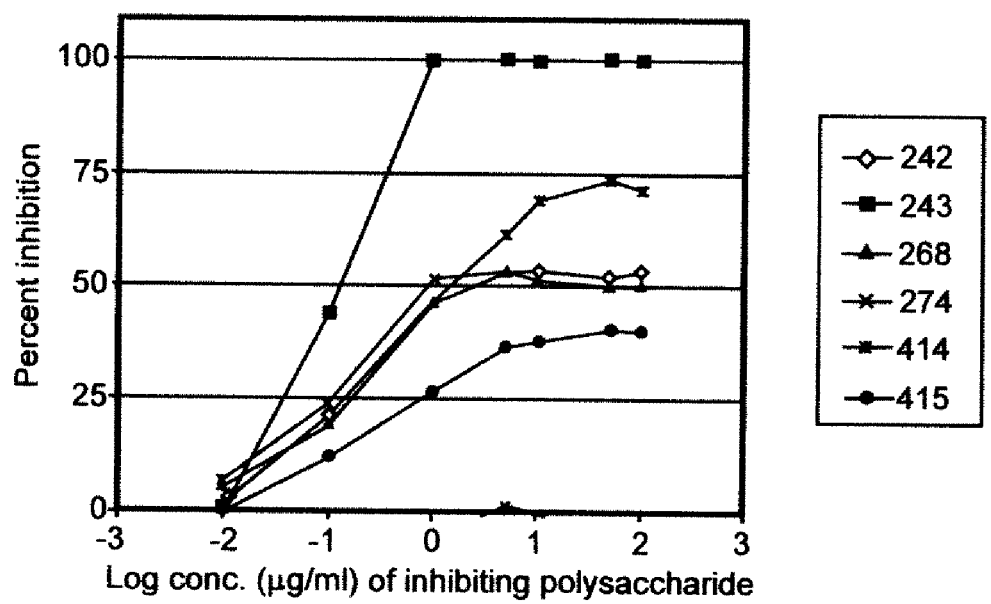

Purified MynC was used in in vitro assays containing the serogroup A wild type or mynC mutant CPS as the substrate and (acetyl-1-$^{14}$C)-coenzyme A as the acetyl donor. Autoradiography of the CPSs (FIG. 4) revealed that MynC transferred the $^{14}$C labeled acetyl group from acetyl CoA to the non-acetylated CPS of the mynC mutant (lanes 5-8, FIG. 4). Interestingly, MynC was also capable of further O-acetylating the wild type CPS (lane 4, FIG. 4). MynC recognized the serogroup A CPS but not serogroup B or serogroup C CPSs (lanes 2 and 3, FIG. 4). Finally, the acetyltransferase activity was not due to minor contaminating E. coli proteins left after purification, as the lysate of the vector construct alone did not exhibit activity (lanes 9 and 10, FIG. 4). MynC activity was concentration-dependent (FIG. 5A) when the amount of CPS substrate and the acetyl donor were constant. The decrease in the estimated activity over 2-3 h time point could be due to the possible degradation of the CPS polymer at the reaction condition that had been removed in 80% ethanol washes. The enzyme seems to be inactive in the extreme pH conditions of less than 5 and greater than 10. The optimal pH for the MynC activity was 5.8 to 7.0 (FIG. 5C). The $Mg^{+2}$ ions present in the in vitro O-acetyltransferase reaction buffer may not be essential for the enzyme activity, as revealed by the assay using citrate, phosphate and borate buffers without these ions, for optimal pH measurements.

An intact copy of mynC under the control of a lac promoter was constructed and sub-cloned into the meningococcal shuttle vector, pYT250, as described in Example 5. The plasmid was transformed into the mynC mutant and the wild type strain to generate strains NmAnpc1 and NmAwtc1, respectively. The wild type strain and the wild type strain over-expressing MynC (NmAwtc1), the mynC mutant, and the complemented strain (NmAnpc1) were grown on GC agar plates with or without IPTG and analyzed by colony immunoblots and ELISAs (FIG. 6A) using the serogroup A capsule-specific monoclonal antibody 14-1-A. The unencapsulated strain F8239, a serogroup A strain which contains point mutations and deletions in mynA (11) was used as a negative control. The wild type and NmAwtc1 meningococci were strongly recognized by mAb 14-1-A, whereas the uncomplemented mynC nonpolar mutant and the capsule negative control strain F8239 did not react with this antibody. The complemented nonpolar mynC mutant strain NmAnpc1 reacted strongly, and the intensity was increased with IPTG induction. These data indicated that a O-acetyl group was a component of the epitope specificity of the monoclonal antibody 14-1-A. The CPS isolated from complemented strain NmAnpc1 was subjected to $^{1}$H NMR analyses which revealed (FIG. 2C) the restoration of O-acetylation in the polymer. When compared by the relative integration values of H2 resonances of 3-O—Ac and non-O—Ac forms, the level of O-acetylation in the complemented strain, even with IPTG, was less than wild type levels, although the relative ratio (5:1:2) of the acetylated species O-3: O-4: O-3 and 4 was similar to the wild type ratio (4:1:1.7) (Table 4). The mynC mutant CPS O-acetylated in vitro by MynC was recognized by the monoclonal antibody 14-1-A, confirming the importance of O-acetylation in defining the epitope recognized by the antibody.

In summary, quantitative ELISA, $^{1}$H NMR and colorimetric assays on the CPS from complemented strain NmAnpc1 revealed that O-acetylation was restored by genetic complementation. Western blot analysis (FIG. 6B) on the whole cell lysates of the MynC over-expressed wild type strain (NmAwtc1), and the complemented mynC mutant (NmAnpc1), using the anti penta-His mAb, was also performed. His-tagged MynC (lanes 4 and 6, FIG. 6B) was visualized in the complemented meningococci under IPTG and this result was correlated with the restoration of O-acetylation in the NmA mutant CPS.

The MynC-complemented strain NmAnpc1 was used to assess the cellular location of MynC in serogroup A meningococci. Western blot analysis of the sub-cellular fractions loaded on the basis of a set amount of starting cells, using $(His)_5$ mAb revealed (FIG. 7A) that MynC was inner membrane-associated. The total membrane and inner membrane components gave strong reactivity, whereas the cytosolic fraction showed weak reaction and outer membrane showed no reaction. To explore the possibility MynC that did not possess any transmembrane domains to be a peripheral protein, various extraction procedures were performed. Treatment of membranes with 6M urea partially stripped off the protein, whereas the other conditions with 1M NaCl or with 1% Tx-100 did not extract the MynC (FIG. 7B) from the total membranes.

Cell surface hydrophobicity, a marker of capsular expression, was measured by hydrophobic interaction column chromatography (23). Approximately 4% of the wild type serogroup A strain F8229 and about 5% of the mynC mutant were retained on the hydrophobic column, indicating overall low cell surface hydrophobicity of both the wild type and the mutant. In contrast, the unencapsulated variant F8239 (>60%) and mynA and mynB mutants (>90%) were retained on the column, indicating high cell surface hydrophobicity. A bactericidal assay using 10% normal human sera was used to assess expression of a functional capsule. Both the wild type parent and the mynC nonpolar mutant were protected from killing. In contrast, the unencapsulated strain F8239 and the mutants of mynA, mynB and mynD were completely killed under these conditions.

O-acetylation is critical for serogroup A *N. meningitidis* CPS immunogenicity and antibody formation (8). The major protective epitope recognized by antibodies induced following vaccination with serogroup A polysaccharide requires O-acetylation. Berry et al. (8) found that bactericidal anti-serogroup A antibodies in the sera of serogroup A polysaccharide vaccinated individuals were specific for O—Ac CPS. The importance of O—Ac in serogroup A capsule immunogenicity was confirmed using O—Ac and non-O—Ac PS and PS-protein conjugates in immunogenicity studies with mice. Interestingly, the serogroup A capsule with or without O-acetylation protected the meningococcus against killing by a low concentration (10%) of normal human serum, e.g. antibody-independent complement mediated killing. O-acetylation may also have a role in the initial stages of colonization and infection by serogroup A *N. meningitidis*. In studies of meningococcal colonization in a mouse model (56), an OAc−mynC mutant showed significantly lower ability to establish colonization compared to the wild type OAc+ strain.

MynC is specific for meningococcal serogroup A {(α1→6) linked N-acetyl-D-mannosamine-1-phosphate} CPS. MynC did not acetylate the sialic acid CPSs of either serogroup B or serogroup C *N. meningitidis*. The in vitro O-acetylation studies indicate that MynC recognized non O-acetylated or the partly O-acetylated CPS assembled polymer as a substrate. Therefore O-acetylation appears to be a near final step of decorating the serogroup A capsule polymer. The cell surface hydrophobicity data and the resistance to killing by normal human sera of the mynC mutant and the wild type parent indicate that the OAc− capsular polymer is surface expressed and functional. Thus, serogroup A capsule expression, transport or prevention of killing by normal human sera does not require O-acetylation.

In summary, MynC is the capsular polysaccharide O-3 and O-4 acetyltransferase of serogroup A of *N. meningitidis*. This approximately 25 kDa inner membrane associated enzyme utilizes acetyl CoA for its activity and belongs to a new subclass of O-acetyltransferases. Study of the OAc deficient mutant confirmed the importance of O-acetylation in serogroup A polysaccharide immunogenicity, but O-acetylation was not required for capsular expression or to protect the meningococcus from killing by normal human sera. O-acetylation by MynC may be important for vaccine development against serogroup A *N. meningitidis*. The ability to achieve O-acetylation of serogroup A polysaccharides used for new and existing meningococcal conjugate and polysaccharide vaccines may be enhanced by this enzyme.

*Neisseria meningitidis* serogroup A capsular polysaccharide (CPS) is composed of a homopolymer of O-acetylated, (α1→6) linked N-acetyl-D-mannosamine (ManNAc)-1-phosphate that is distinct from the capsule structures of the other meningococcal disease causing serogroups B, C, Y and W-135. The serogroup A capsule biosynthetic genetic cassette consists of four ORFs, mynA-D (sacA-D) that are specific to serogroup A, but the function of these genes has not been well characterized. We found that mynC encoded an acetyltransferase that was responsible for the O-acetylation of the CPS of serogroup A. The wild type CPS as revealed by $^1$H NMR had 60 to 70% O-acetylated ManNAc residues that contained acetyl groups at 0-3, with some species acetylated at O-4 and O-3 and O-4. A nonpolar mynC mutant, generated by introducing an aphA-3 kanamycin resistance cassette, produced CPS with no O-acetylation. A serogroup A capsule-specific monoclonal antibody was shown to recognize the wild type O-acetylated CPS but not the CPS of the mynC mutant, which lacked O-acetylation. MynC was C-terminally His-tagged and overexpressed in *E. coli* to obtain the predicted ~26 kDa protein. The acetyltransferase activity of purified MynC was demonstrated in vitro using $^{14}$C labeled acetyl CoA. MynC, O-acetylated the OAc-CPS of the mynC mutant, and further acetylated the wild type CPS of serogroup A but not the CPS of serogroup B or serogroup C meningococci. Genetic complementation of the mynC mutant confirmed the function of MynC as the serogroup A CPS O-3 and O-4 acetyltransferase. MynC is an inner membrane-associated protein of a new subclass of O-acetyltransferases and utilizes acetyl CoA to decorate the D-mannosamine capsule of serogroup A *N. meningitidis*.

Meningococcal serogroups C, Y, W-135 and H also express O-acetylated capsules. Interestingly, the serogroup B CPS is not O-acetylated. The genes indispensable for encoding the putative capsular polysaccharide O-acetyltransferases (OatC, OatWY) responsible for the O-acetylation of meningococcal serogroups C, W-135 and Y, respectively, have been recently identified (5). Other pathogens such as pneumococcal serotype 9V, *Salmonella enterica* serovar typhi Vi, *Staphylococcus aureus* serotypes 5, 8 and *E. coli* K1(6) express O-acetylated capsules. The biological importance of O-acetylation of CPS appears species or subspecies dependent but in some pathogens O-acetylation of capsule is involved in immune recognition (6,7). For serogroup A CPS there is a dramatic reduction in immunogenicity of the polysaccharide observed with removal of the O-acetyl groups by chemical treatment (8).

The general genetic organization of capsular polysaccharide genes of *N. meningitidis* is similar to other bacterial systems such as *Haemophilus influenzae*, *E. coli* K1, etc. that are classified (9,10) as group II capsules. It is composed of unique biosynthesis gene cassette flanked by conserved genes involved in translocation of the CPS. The genetic cassette responsible for the biosynthesis of the serogroup A capsule is comprised of a ~5 kb nucleotide sequence located (FIG. 1) between ctrA, the outer membrane capsule transporter, and galE, the UDP-glucose-4-epimerase (11). Four open reading frames (ORFs 1 to 4 designated as myn A-D or sacA-D) are co-transcribed as an operon (11) and are not found in the genomes of other meningococcal serogroups or in *Neisseria gonorrhoeae*. Separated from ctrA by a 218-bp intergenic region, mynA is predicted to encode a 372-amino acid protein that has homology with the *E. coli* UDP-N-acetyl-D-glucosamine 2-epimerase, MynB is hypothesized to be the capsular polymerase, linking individual UDP-ManNAc monomers together and MynD was predicted to be involved either in CPS transport assembly or in cross-linking of the capsule to the meningococcal cell surface (11). See also U.S. Pat. No. 6,403,306. In the present study we demonstrate that mynC (744-bp) encodes an O-acetyltransferase (247 aa) that transfers acetyl groups to the ManNAc residues of the serogroup A CPS.

Serogroup A *Neisseria meningitidis* is a major cause of endemic meningococcal disease as well as epidemics and pandemics of meningococcal meningitis and meningococcemia in many developing parts of the world. Capsular polysaccharide (CPS) of serogroup A *N. meningitidis* is composed of O-3 or O-4 acetylated a (1→6) linked phospho-ManNAc polymers (1) and is distinct from the chemical structures of the other meningococcal capsular polysaccharides. In serogroup A meningococcal polysaccharide vaccines, O-acetylation of the serogroup A CPS is believed to be important for immunogenicity and protection (8). Other roles of CPS O-acetylation in serogroup A meningococcal pathogenesis have not been defined. This applications discloses the serogroup A CPS O-acetyltransferase gene; and the genes involved in meningococcal sialic acid capsule O-acetylation have also been identified (5). Further, O-acetylation in serogroup A and the other meningococcal serogroups' CPS patterns have been extensively elucidated and investigated by $^{13}$C NMR and $^1$H NMR experiments (3, 61, 28).

The *N. meningitidis* serogroup A CPS biosynthesis genetic cassette is comprised of a ~4.7 kb (11) region containing four ORFs—mynA, mynB, mynC and mynD also known as sacA-D. MynC is responsible for the O-3 and O-4 acetylation of ManNAc CPS. A nonpolar mutation in mynC, generated by insertion of the aphA-3 kanamycin resistance cassette, yielded a CPS devoid of O-acetylation. Colony immunoblots, cell surface hydrophobicity studies and capsule precipitation procedures revealed that the nonpolar mynC mutant (mynC:: aphA-3) surface expressed similar amounts of capsular polysaccharide to the wild-type parent. In this study, the serogroup A encapsulated wild-type parent F8229 (11), an isogenic OAc− nonpolar encapsulated mutant mynC::aphA3 and the unencapsulated mynA or mynB mutants of this strain and the serogroup A capsule deficient strain F8239 were used.

The role of O-acetylation and CPS in the ability of serogroup A meningococci to colonize the nasopharynx of outbred adult Swiss Webster mice was tested. This model has previously been used to define a role of serogroup B capsule in meningococcal colonization. Mice (5/group) were inoculated with $10^7$ CFU of meningococci intra-nasally and were followed for five days with nasopharyngeal washes and cultures of these washes. The wild-type parent (F8229 CAP+/OAc+) effectively colonized 75% of mice, whereas the mynC CAP+/OAc− mutant initially colonized 50%. By day 2, 15% of mice remained colonized with the mynC CAP+/OAc− mutant, whereas with the CAP+/OAc+ wild-type parent, 60% of mice remained colonized. By day 3, colonization of all mice inoculated with the mynC CAP+/OAc− mutant was lost. In contrast, 22-30% of mice inoculated with the wild-type parent remained colonized through the five days of observation (p=0.031 paired Student's t-Test). The unencapsulated serogroup A strain F8239 (23) and the unencapsulated mynA mutant failed to colonize the mice at any time point, indicating a requirement of serogroup A CPS in establishing colonization. Further, the mynC CAP+/OAc− mutant was impaired in the ability to maintain nasopharyngeal colonization when compared to the wild-type parent, suggesting that O-acetylation of the serogroup A CPS may play a role in promoting persistent meningococcal colonization.

The role of serogroup A CPS O-acetylation in protecting the meningococci from killing by pooled normal human sera was also investigated. In serum bactericidal activity assays (24), the wild-type parent and the mynC CAP+/OAc− mutant survived in 10% normal human sera (final concentration, v/v). In contrast, the unencapsulated mynA and mynB mutants of this strain were rapidly and completely killed (FIG. 9) by the same 10% normal human serum. In complement inactivated normal human serum (56° C., 30 min), both encapsulated and unencapsulated meningococci survived (grey bars). Both the CAP+/OAc+ wild-type and the CAP+/OAc− mynC mutant were sensitive (>99% killing) to 25% and 50% (v/v) normal human sera. These results indicated that the O-acetylation did not enhance or diminish the protection provided to meningococci by the serogroup A capsule against complement-mediated bactericidal activity of normal human sera.

To investigate the role of O-acetylation of capsule in serogroup A meningococcal vaccines, CPS of the CAP+/OAc+ wild-type parent and the CAP+/OAc− mynC mutant were prepared and standardized. These preparations were used in inhibition ELISAs in which six well-standardized post vaccine sera (designated 242, 243, 268, 274, 414, 415) from serogroup A polysaccharide vaccinated individuals (Menimmune®) were tested. OAc− serogroup A CPS competitively inhibited significantly less antibody than the wild-type CPS (FIG. 10A-10B) in five of the six sera tested. At the highest concentrations of capsule used for inhibition (100 μg), OAc− CPS was unable to inhibit one sera (274) did inhibit one serum (243), and only incompletely inhibited (40-74%) four of the other sera (242, 268, 414, 415). In contrast, the OAc+ CPS inhibited 75% to 100% of serum bactericidal activity of all six samples. These data confirmed the importance of O-acetylation as a major epitope of the serogroup A meningococcal polysaccharide-containing vaccines for most but not all individuals.

The importance of serogroup A CPS O-3, O-4 acetylation as a factor in meningococcal colonization, in resistance to killing by normal human sera and in serogroup A polysaccharide containing meningococcal vaccines was addressed in this study. The identification of the serogroup A CPS O-acetyltransferase gene, mynC, has facilitated the generation of an encapsulated mutant devoid of O-acetylation. The OAc-mutant, its parent and other isogenic mutants of this strain permitted insights into the role of O-acetylation in serogroup A biology.

Colonization of the human nasopharynx is an essential step in meningococcal pathogenesis (62). The complete failure to establish nasopharyngeal colonization of mice by serogroup A unencapsulated mutants indicates a role of the serogroup A capsule in the initial pathogenic events after meningococcal acquisition in the upper respiratory tract. A similar advantage in promoting nasopharyngeal colonization has been previously shown for the serogroup B capsule. Both of these results may be correlated with a protective role of capsule against elimination of meningococci by human host defenses at mucosal surfaces at the time of initial acquisition. The impaired ability of the mynC CAP+/OAc− to maintain colonization, compared to the wild-type parent suggests an additional role of serogroup A capsule O-acetylation in meningococcal nasopharyngeal colonization of the nasopharynx. The bulky O-acetyl groups might facilitate initial adherence interactions with the nasopharyngeal mucosal epithelial surface or further enhance resistance to mucosal host defenses. O-acetylation of the exopolysaccharide alginate in *Pseudomonas aeruginosa* has been shown to contribute to biofilm and microcolony formation and to facilitate resistance to opsonic phagocytosis (35, 36). Also, O-acetylation of rhizobial Nod factors defines host specificity and is critical for the formation of the preinfection thread and the root nodule in *Rhizobium*-legume symbiosis (37, 38, 39).

The presence of capsule expressed on the surface of serogroup A meningococci was important for protection against complement-mediated bactericidal activity of normal human sera. Mutants such as mynA and mynB that lack CPS were rapidly killed by all concentrations of normal human sera. However, serogroup A capsule O-acetylation was not required for or enhanced this protection. Both the encapsulated parent and OAc− mutant survived similarly in low concentrations of human sera. Low concentrations of sera (10% or less) are usually associated with antibody-mediated classical complement pathway activation (63) rather than alternative or possibly MBL lectin pathway activation requiring higher concentrations of human sera.

Despite the disappearance of exposure to serogroup A *N. meningitidis* in the United States and other industrialized countries, many individuals from these areas have serum bactericidal activity against serogroup A meningococci. This may be due to antibodies directed at cross-reactive serogroup A capsule-like epitopes present on *Bacillus pumilus, Enterococcus faecalis* and other commensal bacteria (64) or antibodies to noncapsular outer membrane epitopes, or components of the meningococcal surface that lead to complement activation. In a recent study, Granoff and Amir (65) found a high prevalence of cross-reacting serogroup A capsular antibodies in bactericidal sera from North America but only a small number of these bactericidal sera were directly inhibited by purified group A CPS. Complement activation by mannose-binding lectin (MBL) attachment to the Opa and PorB proteins of *N. meningitidis* has been reported. Thus, in our study, serogroup A CPS, regardless of O-3 or O-4 acetylation, was protective against low levels of classical pathway complement activation, but serogroup A meningococci, regardless of O-acetylation, were killed by higher concentrations of normal human sera.

Berry et al. (8) previously studied the effects of *N. meningitidis* serogroup A capsular O-acetylation on development of immune responses to serogroup A CPS. Using chemical removal of O-acetyl groups, they found that a majority of antibodies generated by vaccination with serogroup A CPS were specific for epitopes involving O-acetyl groups and that a dramatic reduction in immunogenicity was associated with removal of these groups. Similarly monoclonal antibodies against the O-acetylated serotype 5 capsule of *S. aureus* are specific for the O-acetyl epitope (66). Among the meningococcal sialic acid capsules, serogroup B meningococci lack O-acetylation, serogroup C meningococci can express O-7 or O-8 acetylation and serogroups W-135 and Y have variable O-7 or O-9 acetylation. In contrast to serogroup A meningococcal O-acetylation, O-acetylation of capsule in meningococcal serogroup C (32), pneumococcal serotype 9V (33) and *E. coli* K1 (67) do not appear essential for the induction of protective antibodies.

Our data indicate that the O-acetyl group is a dominant epitope on the serogroup A CPS in individuals. Other capsular polysaccharides with immuno-dominant O-acetyl epitopes are *S. aureus* serotype 5 (ManANAc O-3) and *Salmonella typhi* VI (GalANAc O-3). Interestingly, in capsules with immuno-dominant acetylation epitopes, the acetylation sites are within the hexose sugar ring (endo-cyclic). In contrast, the O-acetyl epitopes of other capsules including the meningococcal sialic acid C, Y or W-135 capsules (at positions O-7, O-8 or O-9), *E. coli* K1 (at positions O-7, O-9), and the *S. pneumoniae* serotype 9V capsule (ManNAc O-6) that do not contribute to protective immunity are positioned in the exocyclic side chain. Thus, the endo-cyclic position of O-acetylation, may have less mobility compared to an exocyclic side chain location and appears to position the O-acetyl group as a dominant epitope recognized by the human immune system.

In the present study, serogroup A O-acetylation did not enhance or diminish resistance of meningococci to complement-mediated bactericidal activity of normal human serum. However, O-acetylation of the meningococcal serogroup A CPS contributed in an animal model to nasopharyngeal colonization by this serogroup and was a major epitope for antibodies generated by serogroup A CPS vaccination.

Expression refers to the transcription and translation of a structural gene (coding sequence) so that a protein (i.e., expression product) having the biological activity of the O-acetyltransferase of the present invention is synthesized. It is understood that post-translational modification(s) in certain types of recombinant host cells may remove portions of the polypeptide which are not essential to enzymatic activity.

The term expression control sequences refer to DNA sequences that control and regulate the transcription and translation of another DNA sequence (i.e., a coding sequence). A coding sequence is operatively linked to an expression control sequence when the expression control sequence controls and regulates the transcription and translation of that coding sequence. Expression control sequences include, but are not limited to, promoters, enhancers, promoter-associated regulatory sequences, transcription termination and polyadenylation sequences, and their positioning and use is well understood by the ordinary skilled artisan. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene. The combination of the expression control sequences and the O-acetyltransferase coding sequence form the O-acetyltransferase expression cassette.

As used herein, an exogenous or heterologous nucleotide sequence is one which is not in nature covalently linked to a particular nucleotide sequence, e.g., an O-acetyltransferase coding sequence. Examples of exogenous nucleotide sequences include, but are not limited to, plasmid vector sequences, expression control sequences not naturally associated with particular O-acetyltransferase coding sequences, and viral or other vector sequences. A non-naturally occurring DNA molecule is one which does not occur in nature, and it is thus distinguished from a chromosome, or example. As used herein, a non-naturally occurring DNA molecule comprising a sequence encoding an expression product with O-acetyltransferase activity is one which comprises said coding sequence and sequences which are not associated therewith in nature.

Similarly, as used herein an exogenous gene is one which does not naturally occur in a particular recombinant host cell but has been introduced in using genetic engineering techniques well known in the art. An exogenous gene as used herein can comprise an O-acetyltransferase coding sequence expressed under the control of an expression control sequence not associated in nature with said coding sequence.

Another feature of this invention is the expression of the sequences encoding O-acetyltransferase. As is well-known in the art, DNA sequences may be expressed by operatively linking them to an expression control sequence in an appropriate expression vector and employing that expression vector to transform an appropriate host cell.

A wide variety of host/expression vector combinations may be employed in expressing the DNA sequences of this invention. Useful expression vectors, for example, may consist of segments of chromosomal, nonchromosomal and synthetic DNA sequences. Suitable vectors include derivatives of SV40 and known bacterial plasmids, e.g., *Escherichia coli* plasmids colE1, pCR1, pBR322, pMB9 and their derivatives, plasmids such as RP4; phage DNAs, e.g., M13 derivatives, the numerous derivatives of phage λ, e.g., λgt11, and other phage DNA; yeast plasmids derived from the 2μ circle; vectors useful in eukaryotic cells, such as insect or mammalian cells; vectors derived from combinations of plasmids and phage DNAs, such as plasmids that have been modified to employ phage DNA or other expression control sequences; baculovirus derivatives; and the like. For mammalian cells there are a number of well-known expression vectors available to the art.

Any of a wide variety of expression control sequences may be used in these vectors to express the DNA sequences of this invention. Such useful expression control sequences include, for example, the early and late promoters of SV40 or adenovirus for expression in mammalian cells, the lac system, the trp system, the tac or trc system, the major operator and promoter regions of phage λ, the control regions of fd coat protein, the promoter for 3-phosphoglycerate kinase of phosphatase (e.g., pho5), the promoters of the yeast α-mating factors, and other sequences known to control the expression of genes of prokaryotic or eukaryotic cells or their viruses, and various combinations thereof. The skilled artisan understands which expression control sequences are appropriate to particular vectors and host cells.

A wide variety of host cells are also useful in expressing the DNA sequences of this invention. These hosts may include well-known prokaryotic and eukaryotic hosts, such as strains of *E. coli, Pseudomonas, Bacillus, Streptomyces*, fungi such as yeasts, and animal cells, such as Chinese Hamster Ovary (CHO), R1.1, B-W and L-M cells, African Green Monkey kidney cells (e.g., COS 1, COS-7, BSC1, BSC40, and BMT10), insect cells (e.g., Sf9), and human cells and plant cells in culture.

It is understood that not all combinations of vector, expression control sequence and host cell will function equally well to express the DNA sequences of this invention. However, one skilled in the art will be able to select the proper vector, expression control sequence, and host cell combination without undue experimentation to accomplish the desired expression without departing from the scope of this invention.

In selecting a suitable expression control sequence, a variety of factors will normally be considered. These include, for example, the relative strength of the promoter, its controllability, and its compatibility with the particular DNA sequence or gene to be expressed, e.g., with regard to potential secondary structure. Suitable hosts will be selected by consideration of factors including compatibility with the chosen vector, secretion characteristics, ability to fold proteins correctly, and fermentation requirements, as well as any toxicity to the host of the product encoded by the DNA sequences to be expressed, and the ease of purification of the expression products. The practitioner will be able to select the appropriate host cells and expression mechanisms for a particular purpose.

Several strategies are available for the isolation and purification of recombinant O-acetyltransferase after expression in a host system. One method involves expressing the proteins in bacterial cells, lysing the cells, and purifying the protein by conventional means. Alternatively, one can engineer the DNA sequences for secretion from cells. An O-acetyltransferase protein can be readily engineered to facilitate purification and/or immobilization to a solid support of choice. For example, a stretch of 6-8 histidines can be engineered through polymerase chain reaction or other recombinant DNA technology to allow purification of expressed recombinant protein over a nickel-charged nitrilotriacetic acid (NTA) column using commercially available materials. Other oligopeptide "tags" which can be fused to a protein of interest by such techniques include, without limitation, strep-tag (Sigma-Genosys, The Woodlands, Tex.) which directs binding to streptavidin or its derivative streptactin (Sigma-Genosys); a glutathione-S-transferase gene fusion system which directs binding to glutathione coupled to a solid support (Amersham Pharmacia Biotech, Uppsala, Sweden); a calmodulin-binding peptide fusion system which allows purification using a calmodulin resin (Stratagene, La Jolla, Calif.); a maltose binding protein fusion system allowing binding to an amylose resin (New England Biolabs, Beverly, Mass.); and an oligo-histidine fusion peptide system which allows purification using a $Ni^{2+}$-NTA column (Qiagen, Valencia, Calif.).

Coding sequences which are synonymous to the coding sequence provided in SEQ ID NO:1 are within the scope of the present invention, as are sequences encoding O-acetyltransferases carrying out the same O-3 and O-4 acetylations of *Neisseria meningitidis* capsular polysaccharides, and where those sequences encode an O-acetyltransferases with at least 80% amino acid sequence identity with that of SEQ ID NO:2. All integers between 80 and 100% are included within the scope of the present invention in this context. In calculations of amino acid sequence identify, gaps inserted to optimize alignment are treated as mismatches.

O-acetyltransferase coding sequences from various *N. meningitidis* strains have significant sequence homology to the exemplified O-acetyltransferase coding sequences, and the encoded enzymes have a high degree of amino acid sequence identity as disclosed herein. It is obvious to one normally skilled in the art that nonexemplified clones and PCR amplification products can be readily isolated using standard procedures and the sequence information provided herein. The ordinary skilled artisan can utilize the exemplified sequences provided herein, or portions thereof, preferably at least 25-30 bases in length, in hybridization probes to identify cDNA (or genomic) clones encoding O-acetyltransferase, where there is at least 70% sequence homology to the probe sequence using appropriate art-known hybridization techniques. The skilled artisan understands that the capacity of a cloned cDNA to encode functional O-acetyltransferase enzyme can be readily tested as taught herein.

Hybridization conditions appropriate for detecting various extents of nucleotide sequence homology between probe and target sequences and theoretical and practical consideration are given, for example in B. D. Hames and S. J. Higgins (1985) *Nucleic Acid Hybridization*, IRL Press, Oxford, and in Sambrook et al. (1989) supra. Under particular hybridization conditions the DNA sequences of this invention will hybridize to other DNA sequences having sufficient homology, including homologous sequences from different species. It is understood in the art that the stringency of hybridization conditions is a factor in the degree of homology required for hybridization. The skilled artisan knows how to manipulate the hybridization conditions so that the stringency of hybridization is at the desired level (high, medium, low). If attempts to identify and isolate the O-acetyltransferase gene from another *N. meningitidis* strain fail using high stringency conditions, the skilled artisan will understand how to decrease the stringency of the hybridization conditions so that a sequence with a lower degree of sequence homology will hybridize to the sequence used as a probe. The choice of the length and sequence of the probe is readily understood by the skilled artisan.

The DNA sequences of this invention refer to DNA sequences prepared or isolated using recombinant DNA techniques. These include cDNA sequences, sequences isolated using PCR, DNA sequences isolated from their native genome, and synthetic DNA sequences. As used herein, this term is not intended to encompass naturally-occurring chromosomes or genomes. These sequences can be used to direct recombinant synthesis of O-acetyltransferase for enzymatic acetylation of isolated capsular polysaccharide, especially from *N. meningitidis* Serogroup A strains.

Isolated capsular polysaccharide is separated from the cells and culture medium from which it was produced. Further purification is optional and within the realm of the skilled artisan.

In the present context, an in vitro enzymatic reaction, especially O-3 and O-4 acetylation of Serogroup A *N. meningitidis* capsular polysaccharide, is carried out in the absence of whole, live cells. The enzyme source can be a purified or partly purified enzyme or it can be present in a cell extract, recombinantly produced or otherwise, although greater amounts per cell are produced through recombinant DNA technology.

It is well-known in the biological arts that certain amino acid substitutions can be made within a protein without affecting the functioning of that protein. Preferably such substitutions are of amino acids similar in size and/or charge properties. For example, Dayhoff et al. (1978) in *Atlas of Protein Sequence and Structure*, Volume 5, Supplement 3, Chapter 22, pages 345-352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

It will be a matter of routine experimentation for the ordinary skilled artisan to use the DNA sequence information presented herein to optimize O-acetyltransferase expression in a particular expression vector and cell line for a desired purpose. A cell line genetically engineered to contain and express an O-acetyltransferase coding sequence is useful for the recombinant expression of protein products with the characteristic enzymatic activity of the specifically exemplified enzyme. Any means known to the art can be used to introduce an expressible O-acetyltransferase coding sequence into a cell to produce a recombinant host cell, i.e., to genetically engineer such a recombinant host cell. Recombinant host cell lines which express high levels of O-acetyltransferase are useful as sources for the purification of this enzyme, especially for in vitro acetylation of isolated capsular polysaccharides, desirably those from N. meningitidis Serogroup A. The amino acids which occur in the various amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, H is, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Try, Tryptophan; Y, Tyr, Tyrosine.

A protein is considered an isolated protein if it is a protein isolated from a host cell in which it is recombinantly produced. It can be purified or it can simply be free of other proteins and biological materials with which it is associated in nature.

An isolated nucleic acid is a nucleic acid the structure of which is not identical to that of any naturally occurring nucleic acid or to that of any fragment of a naturally occurring genomic nucleic acid spanning more than three separate genes. The term therefore covers, for example, a DNA which has the sequence of part of a naturally occurring genomic DNA molecule but is not flanked by both of the coding or noncoding sequences that flank that part of the molecule in the genome of the organism in which it naturally occurs; a nucleic acid incorporated into a vector or into the genomic DNA of a prokaryote or eukaryote in a manner such that the resulting molecule is not identical to any naturally occurring vector or genomic DNA; a separate molecule such as a cDNA, a genomic fragment, a fragment produced by polymerase chain reaction (PCR), or a restriction fragment; and a recombinant nucleotide sequence that is part of a hybrid gene, i.e., a gene encoding a fusion protein. Specifically excluded from this definition are nucleic acids present in mixtures of DNA molecules, transformed or transfected cells, and cell clones, e.g., as these occur in a DNA library such as a cDNA or genomic DNA library.

In the present context, a promoter is a DNA region which includes sequences sufficient to cause transcription of an associated (downstream) sequence. The promoter may be regulated, i.e., not constitutively acting to cause transcription of the associated sequence. If inducible, there are sequences present which mediate regulation of expression so that the associated sequence is transcribed only when an inducer molecule is present in the medium in or on which the organism is cultivated.

One DNA portion or sequence is downstream of second DNA portion or sequence when it is located 3' of the second sequence. One DNA portion or sequence is upstream of a second DNA portion or sequence when it is located 5' of that sequence.

One DNA molecule or sequence and another are heterologous to another if the two are not derived from the same ultimate natural source. The sequences may be natural sequences, or at least one sequence can be designed by man, as in the case of a multiple cloning site region. The two sequences can be derived from two different species or one sequence can be produced by chemical synthesis provided that the nucleotide sequence of the synthesized portion was not derived from the same organism as the other sequence.

An isolated or substantially pure nucleic acid molecule or polynucleotide is an O-acetyltransferase-encoding polynucleotide which is substantially separated from other polynucleotide sequences which naturally accompany it on the *N. meningitidis* chromosome. The term embraces a polynucleotide sequence which has been removed from its naturally occurring environment, and includes recombinant or cloned DNA isolates, chemically synthesized analogues and analogues biologically synthesized by heterologous systems.

A polynucleotide is said to encode a polypeptide if, in its native state or when manipulated by methods known to those skilled in the art, it can be transcribed and/or translated to produce the polypeptide or a fragment thereof. The anti-sense strand of such a polynucleotide is also said to encode the sequence.

A nucleotide sequence is operably linked when it is placed into a functional relationship with another nucleotide sequence. For instance, a promoter is operably linked to a coding sequence if the promoter effects its transcription or expression. Generally, operably linked means that the sequences being linked are contiguous and, where necessary to join two protein coding regions, contiguous and in reading frame. However, it is well known that certain genetic elements, such as enhancers, may be operably linked even at a distance, i.e., even if not contiguous.

The term recombinant polynucleotide refers to a polynucleotide which is made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

Polynucleotide probes include an isolated polynucleotide attached to a label or reporter molecule and may be used to identify and isolate other O-acetyltransferase coding sequences, for example, those from others strains of *N. meningitidis*. Probes comprising synthetic oligonucleotides or other polynucleotides may be derived from naturally occurring or recombinant single or double stranded nucleic acids or be chemically synthesized. Polynucleotide probes may be labeled by any of the methods known in the art, e.g., random hexamer labeling, nick translation, or the Klenow fill-in reaction, or with fluors or other detectable moieties.

Large amounts of the polynucleotides may be produced by replication in a suitable host cell. Natural or synthetic DNA fragments coding for a protein of interest are incorporated into recombinant polynucleotide constructs, typically DNA constructs, capable of introduction into and replication in a prokaryotic or eukaryotic cell, especially cultured mammalian cells, wherein protein expression is desired. Usually the construct is suitable for replication in a host cell, such as cultured mammalian cell or a bacterium, but a multicellular eukaryotic host may also be appropriate, with or without integration within the genome of the host cell. Commonly used prokaryotic hosts include strains of *Escherichia coli*, although other prokaryotes, such as *Bacillus subtilis* or a pseudomonad, may also be used. Eukaryotic host cells include mammalian cells, yeast, filamentous fungi, plant, insect, amphibian and avian cell lines. Such factors as ease of manipulation, ability to appropriately glycosylate expressed proteins, degree and control of recombinant protein expression, ease of purification of expressed proteins away from cellular contaminants or other factors influence the choice of the host cell.

The polynucleotides may also be produced by chemical synthesis, e.g., by the phosphoramidite method described by Beaucage and Caruthers (1981) *Tetra. Letts.* 22: 1859-1862 or the triester method according to Matteuci et al. (1981) J. Am. Chem. Soc. 103: 3185, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence. DNA constructs prepared for introduction into a prokaryotic or eukaryotic host will typically comprise a replication system (i.e. vector) recognized by the host, including the intended DNA fragment encoding the desired polypeptide, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included where appropriate from secreted polypeptides of the same or related species, which allow the protein to cross and/or lodge in cell membranes or be secreted from the cell.

An appropriate promoter and other necessary vector sequences will be selected so as to be functional in the host. Examples of workable combinations of cell lines and expression vectors are described in Sambrook et al. (1989) vide infra; Ausubel et al. (Eds.) (1995) *Current Protocols in Molecular Biology*, Greene Publishing and Wiley Interscience, New York; and Metzger et al. (1988) *Nature,* 334: 31-36. Many useful vectors for expression in bacteria, yeast, fungal, mammalian, insect, plant or other cells are well known in the art and may be obtained from such vendors as Stratagene, New England Biolabs, Promega Biotech, and others. In addition, the construct may be joined to an amplifiable gene (e.g., DHFR) so that multiple copies of the gene may be made. For appropriate enhancer and other expression control sequences, see also *Enhancers and Eukaryotic Gene Expression*, Cold Spring Harbor Press, N.Y. (1983). While such expression vectors may replicate autonomously, they may less preferably replicate by being inserted into the genome of the host cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend on the host cell; appropriate markers for different hosts are known in the art.

Recombinant host cells, in the present context, are those which have been genetically modified to contain an isolated DNA molecule of the instant invention. The DNA can be introduced by any means known to the art which is appropriate for the particular type of cell, including without limitation, transfection, transformation, lipofection or electroporation.

It is recognized by those skilled in the art that the DNA sequences may vary due to the degeneracy of the genetic code and codon usage. All (synonymous) DNA sequences which code for the O-acetyltransferase protein are included in this invention, including the DNA sequence as given in FIG. 8A. Also contemplated are coding sequences which encode an O-acetyltransferase as taught herein with at least 80% amino acid sequence identity to that of SEQ ID NO:2.

Additionally, it will be recognized by those skilled in the art that allelic variations may occur in the DNA sequences which will not significantly change activity of the amino acid sequences of the peptides which the DNA sequences encode. All such equivalent DNA sequences are included within the scope of this invention and the definition of the regulated promoter region. The skilled artisan will understand that the sequence of the exemplified O-acetyltransferase protein and the nucleotide sequence encoding it can be used to identify and isolate additional, nonexemplified nucleotide sequences which are functionally equivalent to the sequences given FIG. 8A.

Hybridization procedures are useful for identifying polynucleotides with sufficient homology to the subject coding sequence to be useful as taught herein. The particular hybridization technique is not essential to the subject invention. As improvements are made in hybridization techniques, they can be readily applied by one of ordinary skill in the art.

A probe and sample are combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical, or completely complementary if the annealing and washing steps are carried out under conditions of high stringency. The probe's detectable label provides a means for determining whether hybridization has occurred.

In the use of the oligonucleotides or polynucleotides as probes, the particular probe is labeled with any suitable label known to those skilled in the art, including radioactive and non-radioactive labels. Typical radioactive labels include $^{32}$P, $^{35}$S, or the like. Non-radioactive labels include, for example, ligands such as biotin or thyroxine, as well as enzymes such as hydrolases or peroxidases, or a chemiluminescent reagent such as luciferin, or fluorescent compounds like fluorescein and its derivatives. Alternatively, the probes can be made inherently fluorescent as described in International Application No. WO 93/16094.

Various degrees of stringency of hybridization can be employed. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well know in the art, as described, for example in Keller, G. H., M. M. Manak (1987) *DNA Probes*, Stockton Press, New York, N.Y., pp. 169-170, hereby incorporated by reference.

As used herein, moderate to high stringency conditions for hybridization are conditions which are particularly advantageous. An example of high stringency conditions are hybridizing at 68° C. in 5×SSC/5×Denhardt's solution/0.1% SDS, and washing in 0.2×SSC/0.1% SDS at room temperature. An example of conditions of moderate stringency are hybridizing at 68° C. in 5×SSC/5×Denhardt's solution/0.1% SDS and washing at 42° C. in 3×SSC. The parameters of temperature and salt concentration can be varied to achieve the desired level of sequence identity between probe and target nucleic acid. See, e.g., Sambrook et al. (1989) vide infra or Ausubel et al. (1995) *Current Protocols in Molecular Biology*, John Wiley & Sons, NY, N.Y., for further guidance on hybridization conditions.

Specifically, hybridization of immobilized DNA in Southern blots with $^{32}$P-labeled gene specific probes is performed according to standard methods (Maniatis et al.) In general, hybridization and subsequent washes were carried out under moderate to high stringency conditions that allowed for detection of target sequences with homology to the exemplified sequence. For double-stranded DNA gene probes, hybridization can be carried out overnight at 20-25° C. below the melting temperature (Tm) of the DNA hybrid in 6×SSPE 5×Denhardt's solution, 0.1% SDS, 0.1 mg/ml denatured DNA. The melting temperature is described by the following formula (Beltz, G. A., Jacobe, T. H., Rickbush, P. T., Chorbas, and F. C. Kafatos (1983) *Methods of Enzymology*, R. Wu, L, Grossman and K Moldave (eds) Academic Press, New York 100:266-285).

$$Tm=81.5° C.+16.6 \text{ Log } [Na+]+0.41(+G+C)-0.61(\% \text{ formamide})-600/\text{length of duplex in base pairs.}$$

Washes are typically carried out as follows: twice at room temperature for 15 minutes in 1×SSPE, 0.1% SDS (low stringency wash), and once at TM-20° C. for 15 minutes in 0.2× SSPE, 0.1% SDS (moderate stringency wash).

For oligonucleotide probes, hybridization is carried out overnight at 10-20° C. below the melting temperature (Tm) of the hybrid 6×SSPE, 5×Denhardt's solution, 0.1% SDS, 0.1 mg/ml denatured DNA. Tm for oligonucleotide probes is determined by the following formula: TM(° C.)=2(number T/A base pairs+4(number G/C base pairs) (Suggs, S. V. et al. (1981) *ICB-UCLA Symp. Dev. Biol. Using Purified Genes*, D. D. Brown (ed.), Academic Press, New York, 23:683-693).

Washes are typically carried out as follows: twice at room temperature for 15 minutes 1×SSPE, 0.1% SDS (low stringency wash), and once at the hybridization temperature for 15 minutes in 1×SSPE, 0.1% SDS (moderate stringency wash).

In general, salt and/or temperature can be altered to change stringency. With a labeled DNA fragment>70 or so bases in length, the following conditions can be used: Low, 1 or 2×SSPE, room temperature; Low, 1 or 2×SSPE, 42° C.; Moderate, 0.2× or 1×SSPE, 65° C.; and High, 0.1×SSPE, 65° C.

Duplex formation and stability depend on substantial complementarity between the two strands of a hybrid, and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, and those methods are known to an ordinarily skilled artisan. Other methods may become known in the future.

Thus, mutational, insertional, and deletional variants of the disclosed nucleotide sequences can be readily prepared by methods which are well known to those skilled in the art. These variants can be used in the same manner as the exemplified primer sequences so long as the variants have substantial sequence homology with the original sequence. As used herein, substantial sequence homology refers to homology which is sufficient to enable the variant polynucleotide to function in the same capacity as the polynucleotide from which the probe was derived. Preferably, this homology is greater than 80%, more preferably, this homology is greater than 85%, even more preferably this homology is greater than 90%, and most preferably, this homology is greater than 95%. The degree of homology or identity needed for the variant to function in its intended capacity depends upon the intended use of the sequence. It is well within the skill of a person trained in this art to make mutational, insertional, and deletional mutations which are equivalent in function or are designed to improve the function of the sequence or otherwise provide a methodological advantage.

Polymerase Chain Reaction (PCR) is a repetitive, enzymatic, primed synthesis of a nucleic acid sequence. This procedure is well known and commonly used by those skilled in this art (see, e.g., Mullis, U.S. Pat. Nos. 4,683,195, 4,683, 202, and 4,800,159; Saiki et al. (1985) *Science* 230:1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

It is well known in the art that the polynucleotide sequences of the present invention can be truncated and/or mutated such that certain of the resulting fragments and/or mutants of the original full-length sequence can retain the desired characteristics of the full-length sequence. A wide variety of restriction enzymes which are suitable for generating fragments from larger nucleic acid molecules are well known. In addition, it is well known that Bal31 exonuclease can be conveniently used for time-controlled limited digestion of DNA. See, for example, Maniatis (1982) *Molecular Cloning: A Laboratory Manual*, Cold Spring Harbor Laboratory, New York, pages 135-139, incorporated herein by reference. See also Wei et al. (1983 *J. Biol. Chem.* 258:13006-13512. By use of Bal31 exonuclease (commonly referred to as "erase-a-base" procedures), the ordinarily skilled artisan can remove nucleotides from either or both ends of the subject nucleic acids to generate a wide spectrum of fragments which are functionally equivalent to the subject nucleotide sequences. One of ordinary skill in the art can, in this manner, generate hundreds of fragments of controlled, varying lengths from locations all along the original O-acetyltransferase coding sequence. The ordinarily skilled artisan can routinely test or screen the generated fragments for their characteristics and determine the utility of the fragments as taught herein. It is also well known that the mutant sequences of the full length sequence, or fragments thereof, can be easily produced with site directed mutagenesis. See, for example, Larionov, O. A. and Nikiforov, V. G. (1982) *Genetika* 18(3):349-59; Shortle, D, DiMaio, D., and Nathans, D. (1981) *Annu. Rev. Genet.* 15:265-94; both incorporated herein by reference. The skilled artisan can routinely produce deletion-, insertion-, or substitution-type mutations and identify those resulting mutants which contain the desired characteristics of the full length wild-type sequence, or fragments thereof, i.e., those which retain O-acetyltransferase activity as determined herein.

DNA sequences having at least 80, 90, or at least 95% (and all integers and ranges between 80 and 100%) identity to the recited DNA sequence of FIG. 8A and functioning to encode an O-acetyltransferase protein are within the scope of this invention. Such functional equivalents are included in the definition of an O-acetyltransferase coding sequence. Following the teachings herein and using knowledge and techniques well known in the art, the skilled worker will be able to make a large number of operative embodiments having equivalent DNA sequences to those listed herein without the expense of undue experimentation.

As used herein percent sequence identity of two nucleic acids is determined using the algorithm of Altschul et al. (1997) *Nucl. Acids Res.* 25: 3389-3402; see also Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST programs of Altschul et al. (1990) J. Mol. Biol. 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. (1997) Nucl. Acids. Res. 25:3389-3402. When utilizing BLAST and Gapped BLAST programs, the default parameters of the respective programs (NBLAST and XBLAST) are used. See the National Center for Biotechnology Information on the internet.

In another embodiment, immunogenic compositions for producing polyclonal and/or monoclonal antibodies capable of specifically binding to O-acetyltransferase, O-3 and or O-4 acetylated capsular polysaccharide from *N. meningitidis*, especially Serogroup A, (or fragments thereof) are provided. The term antibody is used to refer both to a homogenous molecular entity and a mixture such as a serum product made up of a plurality of different molecular entities. Monoclonal or polyclonal antibodies, preferably monoclonal, specifically reacting with a particular epitope in a molecule of interest may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice,* 2d ed., Academic Press, New York; and Ausubel et al. (1993) supra. Also, recombinant immunoglobulins may be produced by methods known in the art, including but not limited to, the methods described in U.S. Pat. No. 4,816,567, incorporated by reference herein. Monoclonal antibodies with affinities of $10^8$ $M^{-1}$, preferably $10^9$ to $10^{10}$ or more are preferred.

Antibodies generated against a molecule of interest are useful, for example, as probes for screening DNA expression libraries or for detecting the presence of particular neisserial strains or their isolated capsular polysaccharides in a test sample. Hydrophilic regions of the O-acetyltransferase of the present invention can be identified by the skilled artisan, and peptide antigens can be synthesized and conjugated to a suitable carrier protein (e.g., bovine serum albumin or keyhole limpet hemocyanin) for use in vaccines or in raising antibody specific for LOS biosynthetic proteins. Frequently, the polypeptides and antibodies will be labeled by joining, either covalently or noncovalently, a substance which provides a detectable signal. Suitable labels include but are not limited to radionuclides, enzymes, substrates, cofactors, inhibitors, fluorescent agents, chemiluminescent agents, magnetic particles and the like. United States patents describing the use of such labels include but are not limited to U.S. Pat. Nos. 3,817,837; 3,850,752; 3,939,350; 3,996,345; 4,277,437; 4,275,149; and 4,366,241.

Antibodies specific for the O-3 and/or O-4 acetylated capsular polysaccharide from *N. meningitidis* are useful in preventing disease resulting from neisseriae, especially *N. meningitidis* infections. Such antibodies can be obtained by the methods described above. Because there is some loss of acetyl residues during isolation of the capsular polysaccharide and because there is some loss of immunogenicity of an unacetylated or a poorly acetylated capsular polysaccharide, the quality of a *N. meningitidis* capsular polysaccharide-containing immunogenic composition, it is advantageous to treat a capsular polysaccharide preparation with the O-acetyltransferase of the present invention prior to use in immunogenic compositions, including vaccine compositions.

Compositions and immunogenic preparations, including vaccine compositions comprising in vitro acetylated capsular polysaccharide from *N. meningitidis*, especially Serogroup A *N. meningitides*, and a suitable carrier therefor are provided. Immunogenic compositions are those which result in specific antibody production when injected into a human or an animal. Such immunogenic compositions are useful, for example, in immunizing a human, against infection by neisserial pathogenic strains, especially those of Serogroup A *N. meningitidis*. The immunogenic preparations comprise an immunogenic amount of an in vitro acetylated capsular polysaccharide preparation derived from a *N. meningitidis* strain, especially Serogroup A, and a suitable carrier.

The immunogenic compositions advantageously further comprise lipooligosaccharide(s), proteins and/or neisserial cells of Serogroup A *N. meningitidis* and optionally, one or more other serological types, including but not limited to any known to the art. It is understand that where whole cells are formulated into the immunogenic composition, the cells are preferably inactivated, especially if the cells are of a virulent strain. Such immunogenic compositions may comprise one or more LOS preparations, or another protein or other immunogenic cellular component. By "immunogenic amount" is meant an amount capable of eliciting the production of antibodies directed against neisserial capsular polysaccharides in an animal or human to which the vaccine or immunogenic composition has been administered.

Immunogenic carriers may be used to enhance the immunogenicity of a component of the immunogenic composition as known to the art. Such carriers include, but are not limited to, proteins and polysaccharides, liposomes, and bacterial cells and membranes. Protein carriers may be joined to the molecule(s) of interest to form fusion proteins by recombinant or synthetic means or by chemical coupling. Useful carriers and means of coupling such carriers to polypeptide antigens are known in the art. The art knows how to administer immunogenic compositions so as to generate protective immunity on the mucosal surfaces of the upper respiratory system, especially the mucosal epithelium of the nasopharynx, where immunity is specific for *N. meningitidis*, as well as protecting other parts of the body.

The immunogenic compositions of the present invention may be formulated by any of the means known in the art. Such vaccines are typically prepared as injectables, either as liquid solutions or suspensions. Solid forms suitable for solution in, or suspension in, liquid prior to injection may also be prepared. The preparation may also, for example, be emulsified, or the protein encapsulated in liposomes.

The active immunogenic ingredients are often mixed with excipients or carriers which are pharmaceutically acceptable and compatible with the active ingredient. Suitable excipients include but are not limited to water, saline, dextrose, glycerol, ethanol, or the like and combinations thereof. The concentration of the immunogenic polypeptide in injectable formulations is usually in the range of 0.2 to 5 mg/ml.

In addition, if desired, the vaccines may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutamMyl-L-alanine-2-(1'-2'-dipahnitoyl-sn-glycero-3-hydroxyphosphoryloxy)-ethylamine (CGP 19835A referred to as MTP-PE); and RIM, which contains three components extracted from bacteria, monophosphoryl lipid A, trehalose dimycolate and cell wall skeleton (MPL+TDM+CWS) in a 2% squalene/TWEEN 80 emulsion (TWEEN 80 is polyoxyethylene sorbitan monooleate). The effectiveness of an adjuvant may be determined by measuring the amount of antibodies directed against the immunogen resulting from administration of the immunogen in vaccines which are also comprised of the various adjuvants. Such additional formulations and modes of administration as are known in the art may also be used.

In vitro acetylated capsular polysaccharide from *N. meningitidis* and advantageously containing cells of *N. meningitidis* may be formulated into immunogenic compositions as neutral or salt forms. Preferably, when cells are used they are of attenuated or avirulent strains, or the cells are killed before use. Pharmaceutically acceptable salts include but are not limited to the acid addition salts (formed with free amino groups of the peptide) which are formed with inorganic acids, e.g., hydrochloric acid or phosphoric acids; and organic acids, e.g., acetic, oxalic, tartaric, or maleic acid. Salts formed with the free carboxyl groups may also be derived from inorganic bases, e.g., sodium, potassium, ammonium, calcium, or ferric hydroxides, and organic bases, e.g., isopropylamine, trimethylamine, 2-ethylamino-ethanol, histidine, and procaine.

The immunogenic preparations of the present invention are administered in a manner compatible with the dosage formulation, and in such amount as will be prophylactically and/or therapeutically effective. The quantity to be administered, which is generally in the range of about 100 to 1,000 μg of in vitro acetylated polysaccharide per dose, more generally in the range of about 1 to 500 μg per dose, depends on the subject to be treated, the capacity of the individual's immune system to synthesize antibodies, and the degree of protection desired. Precise amounts of the active ingredient required to be administered may depend on the judgment of the physician and may be peculiar to each individual, but such a determination is within the skill of such a practitioner.

The vaccine or other immunogenic composition may be given in a single dose or multiple dose schedule. A multiple dose schedule is one in which a primary course of vaccination may include 1 to 10 or more separate doses, followed by other doses administered at subsequent time intervals as required to maintain and or reinforce the immune response, e.g., at 1 to 4 months for a second dose, and if needed, a subsequent dose(s) after several months.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention described herein may be practiced in the absence of any element or elements, limitation or limitations which is not specifically disclosed herein, provided that there would be no anticipation by or obviousness over prior art.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The following definitions are provided to clarify their specific use in the context of the invention. Changes therein and other uses will occur to those skilled in the art, which are encompassed within the spirit of the invention, are defined by the scope of the claims.

All patents and publications mentioned in the specification are indicative of the levels of skill of those skilled in the art to which the invention pertains, and all references cited herein are hereby incorporated by reference to the extent that there is no inconsistency with the present specification.

Monoclonal or polyclonal antibodies, preferably monoclonal, specifically reacting with a polypeptide or protein of interest may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice,* 2d ed., Academic Press, New York; and Ausubel et al. (1993) *Current Protocols in Molecular Biology*, Wiley Interscience, New York, N.Y.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1-4, Plenum Press, New York; and Ausubel et al. (1992) *Current Protocols in Molecular Biology*, Greene/Wiley, New York, N.Y. Abbreviations and nomenclature, where employed, are deemed standard in the field and commonly used in professional journals such as those cited herein.

The specifically exemplified compounds and methods and accessory methods described herein are representative of particular embodiments of the present invention; they are not intended to limit the scope of the invention. Thus, additional embodiments are within the scope of the invention and within the following claims.

EXAMPLES

Example 1

Materials and Bacterial Strains

Bacterial strains, plasmids and primers used in this study are described in Table 1. The serogroup A meningococcal strains were originally isolated during an outbreak in Nairobi, Kenya in 1989 (12) and were provided by the Centers for Disease Control and Prevention (CDC), Atlanta, Ga. Strain F8229 (CDC1750) is encapsulated and was isolated from the cerebrospinal fluid of a patient with meningitis. Strain F8239 (CDC16N3) is an unencapsulated variant originally isolated as a serogroup A strain from the pharynx of an asymptomatic carrier. These strains belong to clonal group III-II and are closely related to strains that have caused epidemics in Saudi Arabia, Chad, Ethiopia and other parts of the world.

Monoclonal antibody 14-1-A (13) against meningococcal serogroup A capsular polysaccharide was provided by Dr. Wendell Zollinger, Walter Reed Army Institute of Research.

Restriction enzymes were purchased from New England Biolabs (Beverly, Mass.). Ni-NTA agarose gravity flow matrix and the Anti-Penta-His monoclonal antibodies were purchased from Qiagen Inc. (Valencia, Calif.). The B-PER 6X-His Fusion protein purification kit was purchased from Pierce (Rockford, Ill.). $^{14}$C-labeled acetyl coenzyme A was purchased from Sigma (St. Louis, Mo.). Automated DNA sequence analysis was performed with the Prism Dye-Deoxy Terminator Cycle Sequencing Kit (Applied Biosystems, Foster City, Calif.), and completed reactions were run on an ABI model 377 automated DNA sequencer.

Example 2

Growth Conditions

Meningococcal strains were grown with 3.5% CO2 at 37° C. on GC base agar (Difco, Detroit, Mich.), supplemented with 0.4% glucose and 0.68 mM Fe (NO3)3, or in GC broth containing the same supplements and 0.043% NaHCO3. BHI medium (37 g/liter brain heart infusion) with 1.25% fetal bovine serum was used when kanamycin selection was required. Antibiotic concentrations (in µg/ml) used for *E. coli* strains were ampicillin, 100, kanamycin, 50, and erythromycin, 300; and for *N. meningitidis* were kanamycin, 80, spectinomycin, 60, erythromycin, 3. *E. coli* DH5α strain, cultured on Luria Bertani (LB) medium, was used for cloning and propagation of plasmids. Meningococci were transformed by the procedure of Janik et al. (14). *E. coli* strains were transformed by electroporation (Gene-pulser Bio-Rad, Hercules, Calif., according to the manufacturer's protocol).

Example 3

Construction of Meningococcal mynC Nonpolar Mutant NmA001

An internal 745-bp fragment of mynC, produced by PCR amplification using primers SE57 and SE61 (11) and the chromosomal DNA of strain F8229 as a template, was cloned into pCR2.1 to yield pGS201. The aphA-3 fragment obtained from pUC18K with EcoR I and HinC II digestion and filled in with Klenow polymerase was inserted into the unique SspI site of mynC in pGS201 to generate pGS202. The correct orientation of aphA-3 was confirmed by colony PCR and direct sequencing analysis of pGS202. A ScaI-linearized pGS202 plasmid was used to transform serogroup A meningococcal strain F8229 to generate NmA001. The correct homologous recombination of the aphA-3 cassette into the mynC coding sequence was confirmed by PCR with cassette-specific primers and chromosomal-specific primers.

Example 4

Overexpression and Purification of Meningococcal MynC

The complete coding sequence of mynC was obtained by PCR amplification using SG005 (NdeI) and SG006 (XhoI) primers (Table 1). The PCR product, digested with NdeI and XhoI, was subsequently cloned into pET20b(+) cut with the same enzymes to yield pGS203 that resulted in a C-terminal (His)$_6$ fusion. pGS203 plasmid was purified and subjected to DNA sequence analysis to confirm the intact mynC sequence and the C-terminal His tag fusion. pGS203 was then transformed into the *E. Coli* expression strain BLR21 (DE3) pLysS. One liter of LB culture of the MynC overexpression strain was induced with 1 mM IPTG for 5 h. The harvested cells were resuspended in 15 ml of lysis buffer (50 mM sodium phosphate, pH 8.0; 300 mM NaCl; 10 mM imidazole; 1% (v/v final concentration) TWEEN 20 (TWEEN 20 is polyoxyethylene sorbitan monolaurate), 1 mM phenylmethylsulfonyl fluoride and 1 mg/ml lysozyme) left on ice for 30 min and sonicated 10 times for 30 s with 30 s cooling intervals. The cell debris was removed by centrifugation at 14,000×g for 15 min at 4° C. The over-expressed protein was purified under native conditions on Ni-NTA (nickel-nitrilotriacetic acid) (Qiagen) matrices following the supplier's protocol with modification in column washing. Briefly, the crude extract was incubated with 2 ml of 50% suspension of Ni-NTA agarose for 1 h before packing into a column. The column was washed with 5 ml each of 10, 20 and 40 mM imidazole in lysis buffer (wash 1, wash 2 and wash 3, respectively) and then eluted with 5 ml of 250 mM imidazole containing buffer. The MynC protein was also extracted and purified, using a Pierce B-PER protein extraction kit (15), containing a lysis reagent with a mild nonionic detergent in 20 mM Tris.HCl (pH 7.5), following the manufacturer's instructions. The purified MynC fractions of either methods were concentrated separately by Centricon YM-3 centrifugal filters (Millipore Corporation, Bedford, Mass.) after SDS-PAGE analysis and dialyzed in storage buffer (50 mM HEPES, pH 7.05, 5 mM $MgCl_2$, 100 mM NaCl and 1 mM EDTA). The protein concentration was determined with BCA protein assay kit (Pierce, Rockford, Ill.) using BSA as standard.

Example 5

Complementation of the NmA001 Mutant

An intact copy of mynC coding sequence under the control of the tac promoter was constructed on a meningococcal shuttle vector. Full-length mynC with a C-terminal His tag was amplified from pGS203 using primers SG007 (HindIII) and SG008 (EcoRI) (Table 1). The amplified PCR product was cloned in pCR 2.1 to yield pGS204. The mynC insert was subsequently released from pGS204 with HindIII and EcoRV digestion and ligated into the HindIII and SmaI sites of pFlag-CTC to generate pGS205, with mynC under the control of the lac promoter. The construct was confirmed by PCR using YT79 and YT80 vector-specific primers. The pGS205 plasmid was then cut with BglI, filled in with Klenow, and ligated into the EcoRV site of the meningococcal shuttle vector, pYT250 ($Erm^R$), yielding pGS206. The pGS206 construct was methylated with HaeIII methylase and the reaction mixture used directly to transform the wild type strain F8229 and the mynC nonpolar mutant NmA001, yielding NmAwtc1 and NmAnpc1, respectively.

Example 6

Meningococcal Membrane and Cytosolic Preparations

Meningococcal membranes and cytosols were separated by the method of Clark et al. (16) from the mynC-complemented meningococcal strain NmAnpc1. Briefly, the 500 ml culture pellet of NmAnpc1 carrying pGS205 (mynC), induced overnight with 1 mM IPTG, was used to produce the inner and outer membrane and cytosol preparations. The pellet was suspended in 2 ml of lysis buffer (1 mM EDTA, 50 mM Tris, 20% sucrose, pH 8.0 with 1 mg/ml lysozyme) and incubated for 30 min at 4° C. Spheroplasts were diluted with 20 ml Tris buffer and were sonicated for three times, each for 30 seconds, in an ice bath with 30 second resting intervals. The cell debris was removed by centrifuging at 10K for 15 min at 4° C. The supernatant was freeze-thawed once at −70° C. before ultracentrifugation at 100,000×g for 90 min at 4° C. The pellet, containing the meningococcal membrane fraction, was washed with Tris buffer. The level of contamination of membrane fraction with cytoplasmic components was assessed by determining the activity of the cytoplasmic enzyme malate dehydrogenase (17) for both fractions. The membrane fractions were 97-98% pure. The cytosolic proteins were precipitated using 5% trichloroacetic acid and suspended in 2 ml of 1 M Tris (pH 6.8). Total membrane was solubilized with 2 ml of 2% N-lauroylsarcosine (sarcosyl) in 10 mM HEPES buffer pH 7.4 and stabilized for 1 h at room temperature using an orbital shaker.

Soluble inner membrane components and insoluble outer membrane components were separated by ultracentrifugation at 100,000×g for 2 h at 4° C. The outer membrane pellet was suspended in 500 µl of 1M Tris (pH 6.8). The diluted inner membrane components were precipitated using 5% trichloroacetic acid, and the pellet thus obtained was suspended in 500 µl of 1M Tris (pH 6.8). Sub-cellular fractions were loaded on PAGE gels based on a set amount of starting 500 ml cell culture pellet (~1×$10^{11}$ cells) and analyzed by western blots.

Membrane solubilization experiments were performed as described (18). Briefly, the membrane pellets were extracted with 5 ml of phosphate buffer (pH 7.6) containing 0.2 mM dithiothreitol, 20% sucrose, 0.2 M KCl, and either 1% Triton X-100, 1 M NaCl, or 6 M urea for 30 min at room temperature (urea), at 30° C. (Tx-100), or on ice (buffer alone, buffer with NaCl). Samples were centrifuged for 1 h at 130,000×g (4° C.) after the extraction. Proteins in the soluble fractions were precipitated using 5% trichloroacetic acid, and the precipitates obtained were washed two times in acetone, dried and re-suspended in 1M Tris (pH 6.8) before an equal volume of 2×SDS-PAGE sample buffer was added.

Example 7

CPS Extraction and Structural Characterization

Capsular polysaccharide was extracted from two liters of meningococcal cultures using the method of Gotschlich et al. (19). Briefly, the overnight cultures were treated with a final concentration of 1% CETLAVLON, a polycationic detergent that precipitates the polyanionic polysaccharides. The precipitate was collected by centrifugation and resuspended in water, and $CaCl_2$ was then added to a final concentration of 1 mM in order to separate the polysaccharide from the detergent. Nucleic acids were precipitated from the solution by adding 25% (v/v) of ethanol followed by centrifugation. CPS in the supernatant was subsequently precipitated using ethanol at a final concentration of 80% (v/v). Contaminating protein, traces of CETAVLON (polycationic detergent) and other low molecular weight contaminants were removed with proteinase K digestion and extensive dialysis against a buffer composed of 10% ethanol, 50 mM NaCl, 5 mM Tris. CPS was further purified using a SEPHACRYL 200 (gel filtration) column with 50 mM ammonium formate elution. Column fractions were tested for neutral sugar using the phenol sulfuric acid assay (20). Void volume fractions were pooled and concentrated by speed vacuuming and analyzed by DOC-PAGE and Alcian blue staining (21).

Example 8

Compositional and NMR Analysis of Capsular Polysaccharides

Compositional analysis of purified CPS was performed on the alditol acetate derivatives of the sugars after removal of the phosphate groups by the HF treatment of the purified NmA CPS. The alditol acetate derivatives were analyzed by the combined gas chromatography/mass spectrometry using 30-m SP2330 capillary column (Supelco) (22).

Lyophilized wild type or mutant capsular polysaccharide powder (5 mg) was dissolved in $D_2O$ (Sigma, 99.999% atom D) to a uniform concentration of 5 mg/ml. Solutions were agitated by vortexing for 10 minutes at room temperature.

Low speed centrifugation (7200×g for 10 min) removed undissolved material. Aliquots (600 µl) of the supernatant were transferred to 5 mm NMR tubes and placed in a sonication bath for 10 minutes to eliminate air bubbles trapped on the inner wall of the NMR tubes.

NMR spectra were acquired on a Varian Unity 500 NMR spectrometer equipped with a 5 mm PFG triple resonance probe, high precision temperature controller (+0.1° C.), and under the control of VNMR version 6.1B, or a Varian Inova 500 spectrometer equipped with a 5 mm PFG inverse detection hetero nuclear probe, running under VNMR version 6.1C and Solaris 2.8. One-dimensional (1-D) proton NMR spectra were collected at 25° C. using a standard one-pulse experiment. The transmitter was set at the HDO frequency (4.78 ppm). Standard spectral acquisition conditions are to collect 64 K data points over a spectral window of 8000 Hz. The acquisition time is 4.096 s and a relaxation delay of 26 s is included, giving a recycle time of 30 s. Typically, 64 scans were averaged. Spectra were Fourier-transformed after applying a 0.2 Hz line broadening function. Integrations were performed using subroutines built into the VNMR software.

Example 9

Hydrophobic Interaction Chromatography

The cell surface hydrophobicity of meningococcal strains was tested using a modified method of Field et al. (23). Disposable plastic columns packed with octyl agarose (Sepharose CL-4B, Sigma) to a height of 2 cm were washed with 10 ml of Buffer A (0.2 M ammonium sulphate in 10 mM sodium phosphate buffer, pH 6.8). Meningococci collected from overnight plate cultures were suspended in phosphate, buffered saline (PBS) to an optical density of 10, and a 100 µl aliquot was gently pipetted onto the surface of the column and eluted with 5 ml Buffer A. A 100 µl cell suspension diluted directly into 5 ml of Buffer A was also prepared as a control. The $OD_{600}$ values of both the column flow through and control samples were determined. Results were calculated as the $OD_{600}$ of the flow through divided by that of the control and expressed as a percentage of cells adsorbed to the column.

Example 10

Serum Bactericidal Assay

A serum bactericidal assay was performed as previously described (24) using pooled normal human serum at 10% final concentration (v/v) with 30 min incubation at 37° C. Heat-inactivated normal human serum was used as a control.

Example 11

Immunoblots

Capsular polysaccharides of the serogroup A wild type and mynC mutant NmA001 were resolved on 15% DOC-PAGE gels and transferred onto PVDF membrane using transfer buffer (25 mM Tris, 192 mM glycine, pH 8.3, 20% methanol). An identical gel was stained with Alcian blue to visualize capsule. Membranes were blocked with 3% BSA in Tris-TWEEN (TWEEN 20 is polyoxyethylene sorbitan monolaurate) buffer (0.5 M Tris, pH7.5, 0.9% NaCl, 0.05% TWEEN-20). Serogroup A capsule-specific monoclonal antibody 14-1-A (13) was used as the primary antibody at a 1:1,000 dilution, while alkaline phosphatase conjugated goat anti-mouse IgG+IgM (Organon Teknika Corporation, West Chester, Pa.) was used at 1:5,000 dilution. All incubations were done at room temperature for 1 hour. Blots were developed in 20 ml of alkaline phosphatase buffer (0.1 M Tris, pH 9.5, 0.1 M NaCl, 0.5 mM $MgCl_2$) containing 40 µl of 10% NBT in 70% DMF and 30 µl of BCIP (50 mg/ml in DMF). Colony immunoblots were processed similarly using nitrocellulose membranes. After the meningococci were lifted, the membranes were allowed to air-dry for 30 min at room temperature and then blocked for 1 hour with 5% BSA in Tris-TWEEN buffer. Protein samples for western blots were resolved by 10% SDS-PAGE and transferred to PVDF membranes as described. Anti-penta-His monoclonal antibodies were used as primary antibodies at 1:1,000 dilutions.

Example 12

Whole Cell ELISA

ELISAs were performed as described (11) with the following modifications: 50 µl aliquots of a 1:9 dilution of meningococcal suspensions ($OD_{550}$=0.1) were applied to microtiter plates and dried overnight at 37° C. Monoclonal antibody 14-1-A was used at a 1:30,000 dilution and alkaline phosphatase-conjugated goat-anti mouse secondary antibody (Organon Teknika Corp. West Chester, Pa.) was used at a 1:10,000 dilution. All incubations were performed at 37° C.

Example 13

Colorimetric Estimation of Capsule O-acetylation

O-acetylation of purified CPSs was measured colorimetrically as described by Hestrin (25). Aliquots of CPS samples (500 µl) were incubated with equal volume of 0.035 M hydroxylamine in 0.75 M NaOH for 10 min at 25° C., and then 1 M of perchloric acid (500 µl) and 70 mM ferric perchlorate in 0.5 M perchloric acid (500 µl) were added. The pink color resulting from the presence of O-acetyl groups was quantified at 500 nm with a known amount of ethyl acetate as the standard.

Example 14

In Vitro O-acetyltransferase Activity

O-acetyltransferase enzyme activity was determined by autoradiography using $^{14}C$ labeled acetyl co-enzyme A as acetyl donor and purified meningococcal CPSs as substrate. In a typical 50 µl reaction volume, 50 µg of CPS, 10 µg of the MynC protein and 0.5 µCi of [$^{14}C$]-acetyl-CoA (0.05 µCi/µl, specific activity 47 µCi/µmol) were incubated in a buffer composed of 10 mM Tris, pH 7.4, 20 mM NaCl, 1 mM $MgCl_2$, and 25 mM EDTA. The reaction mixtures were concentrated to near-dryness after 1 hour incubation at 37° C. and then re-suspended in 10 µl of water and 10 µl of 2× sample buffer. The samples were resolved with 15% DOC-PAGE gels. Gels were incubated with intensifying solution (Dupont) for 30 min before drying under vacuum. The dried gels were exposed to X-ray films at −80° C.

Example 15

Concentration, Time and pH Dependence

A typical 25 µl reaction containing 1 to 6 µg of purified MynC, 0.25 µCi of $^{14}C$ acetyl CoA and 25 µg of OAc− CPS purified from mynC nonpolar mutant in the Tris $MgCl_2$ EDTA buffer noted above were incubated for 1 h at 37° C. After the reaction, the CPS was precipitated with 80% (v/v final concentration) ethanol, and the pellet was washed 3 times with 80% ethanol and air-dried. $^{14}$C acetyl incorporations were measured using liquid scintillant (ScintiSafe Econo 1 Fisher Scientific) and a liquid scintillation analyzer (Packard Tricarb 2500 TR). The amount of $^{14}$C acetyl incorporation into CPS by MynC was determined at 5, 15, 30, 60, 120 and 180 min. At the respective time points, 100 μl of ethanol was added to the 25 μl reaction mixtures (see above) containing 5 μg of purified MynC protein, to precipitate the CPS. The pellets were washed three times with 80% ethanol, air-dried, and the incorporation measured by scintillation counts. The stability of 50 μg triplicate samples of mutant CPS substrate was tested in the reaction condition without the enzyme along these time points by estimating the neutral sugar (20) in the pellets after respective washes. In order to determine the optimal pH for the MynC activity, citrate buffer ranging 4.5 to 6.5, phosphate buffer from pH 5.8 to 8.0 and borate buffer from 8.5 to 10.5 with final salt concentration of 20 mM were used in the 25 μl reaction (see above) noted above with 5 μg of purified MynC. The reaction was incubated for 1 h at 37° C.

TABLE 1

Strains, plasmids, and primers used in this study

| Strains/plasmids/Primers | Description or sequence | Reference/Source |
|---|---|---|
| *N. meningitidis* | | |
| F8229 | *N. meningitidis* serogroup A strain (CDC1750) | (11) |
| NmA001 | NmA with chromosomal mynC::aphA-3 mutation | |
| NmAwtc1 | F8229 carrying pGS205 (mynC) | |
| NmAnpc1 | NmA001 carrying pGS205 (mynC) | |
| *E. coli* | | |
| DH5α | Cloning strain | (57) |
| BLR21(DE3) pLysS | Expression strain | Novagen |
| Plasmids | | |
| pCR 2.1 | TA cloning | Stratagene |
| pUC18 | Cloning vector, Amp$^r$ | (58) |
| pUC18K | Source of aphA-3 (km$^r$) cassette | (59) |
| pFlag-CTC | Cloning vector for FLAG fusion | Sigma |
| pYT250 | Meningococcal shuttle vector (Em$^r$) | (60) |
| pGS201 | SE57-SE61 PCR product cloned into pCR2.1 | |
| pGS202 | aphA-3 cloned into blunted SspI site of pGS201 | |
| pGS203 | Full length mynC obtained from SG005 (NdeI) and SG006 (xhoI) PCR product cloned into NdeI-XhoI digested pET20b | |
| pGS204 | Full length mynC with His-tag obtained from SG007 (HindIII) and SG008 (EcoRI) PCR product cloned into pCR2.1 | |
| pGS205 | HindIII-EcoRV digested fragment of pGS204 ligated with HindIII-SmaI digested fragment of pFlag-CTC | |
| pGS206 | BglI digested fragment of pGS205 subcloned into EcoRV site of pYT250 | |
| Primers | | |
| | 5' → 3' | |
| SE56 | AATCATTTCAATATCTTCACAGCC; SEQ ID NO: 3 | |
| SE57 | TTACCTGAATTTGAGTTGAATGGC; SEQ ID NO: 4 | |
| SE61 | CAAAGGAAGTTACTGTTGTCTGC; SEQ ID NO: 5 | |
| YT79 | CATCATAACGGTTCTGGCAAATATTC; SEQ ID NO: 6 | |
| YT80 | CTGTATCAGGCTGAAAATCTTCTCTC; SEQ ID NO: 7 | |
| SG005 | GAACATATGTTATCTAATTTAAAAAAC; SEQ ID NO: 8 | |
| SG006 | TTACTCGAGATATATATTTTGGATTATGGT; SEQ ID NO: 9 | |
| SG007 | GGAGATATACATAAGCTTTCTAATTTAAAA; SEQ ID NO: 10 | |
| SG008 | AGCGAATTCTCAGTGGTGGTGGTGGTG; SEQ ID NO: 11 | |

TABLE 2

Homology of MynC (247aa)

| Organism | Protein (aa) | Function | Identity (%) | Similarity (%) | Range |
|---|---|---|---|---|---|
| *Caldicellulosiruptor saccharolyticus* | XynC, Acetyl esterase (266) | Xylan degradation | 27 | 45 | 208 |
| *Actinobacillus suis* | Hypothetical protein (410) | Unknown | 33 | 49 | 133 |
| *Bacillus anthracis* | Conserved protein (896) | Unknown | 26 | 45 | 184 |

TABLE 2-continued

Homology of MynC (247aa)

| Organism | Protein (aa) | Function | Identity (%) | Similarity (%) | Range |
|---|---|---|---|---|---|
| Lactococcus lactis | EpsK (152) | EPS biosynthesis | 30 | 44 | 130 |
| Staphylococcus aureus | Cap8I (464) | CPS biosynthesis | 25 | 46 | 119 |

TABLE 3

Proton assignments in ppm of the 3-O—Ac and non-O—Ac CPSs.

| CPS | $CH_3$—NAc | $CH_3$—OAc | H-1 | H-2 | H-3 | H-4 | H-5 | H6/6' |
|---|---|---|---|---|---|---|---|---|
| 3-O—Ac | 2.08 | 2.06/2.10 | 5.46 | 4.61 | 5.20 | 4.01 | 4.14 | 4.20/4.30 |
| Non OAc | 2.08 | — | 5.44 | 4.45 | 4.14 | 3.82 | 4.01 | 4.18/4.24 |

TABLE 4

Relative percentages* of the various CPSs from wild type, mynC

| Strain | 3-O—Ac CPS[a] | 4-O—Ac CPS[b] | 4-OAc CPS[c] | Non-OAc CPS |
|---|---|---|---|---|
| Wild type | 40 | 10 | 17 | 33 |
| mynC::aphA3 | 0 | 0 | 0 | 100 |
| NmAnpc1 | 26 | 4.8 | 8.4 | 61 |

*Calculated from the integration values of the H2 resonances.
[a]O—Ac, O-acetylated.
[b]Based on the assignment of the resonance of the H2 of 4-O—Ac-ManNAc when it is adjacent to a 3-O—Ac-ManNAc residue.
[c]Based on the assignment of the resonance of the H2 of 4-O—Ac-ManNAc when it is adjacent to a non-O—Ac-ManNAc residue.

REFERENCES CITED IN THE SPECIFICATION

1. Liu, T. Y., Gotschlich, E. C., Jonssen, E. K., and Wysocki, J. R. (1971) *J. Biol. Chem.* 246, 2849-2858.
2. Bundle, D. R., Smith. I. C. P., and Jennings. H. J. (1974) *J. Biol. Chem.* 249, 2275-2281.
3. Bhattacharjee, A. K., Jennings, H. J., Kenny, C. P., Martin, A., and Smith, I. C. (1976) *Can. J. Biochem.* 54, 1-8.
4. Bhattacharjee, A. K., Jennings, H. J., Kenny, C. P., Martin, A., and Smith, I. C. P. (1975) *J. Biol. Chem.* 250, 1926-1932.
5. Claus, H., Borrow, R., Achtman, M., Morelli, G., Kantelberg, C., Longworth, E., Frosch, M., and Vogel, U. (2004) *Mol. Microbiol.* 51, 227-239.
6. Orskov, F., Orskov, I., Sutton, A., Schneerson, R., Lin, W., Egan, W., Hoff, G. E., and Robbins, J. B. (1979) *J. Exp. Med.* 149, 669-685.
7. Szu, S. C., Li, X. R., Stone, A. L., and Robbins, J. B. (1991) *Infect. Immun.* 59, 4555-4561.
8. Berry, D. S., Lynn, F., Lee, C. H., Frasch, C. E., and Bash, M. C. (2002) *Infect. Immun.* 70, 3707-3713.
9. Roberts, I. S. (1996) *Annu. Rev. Microbiol.* 50, 285-315.
10. Whitfield, C., and Roberts, I. S. (1999) *Mol. Microbiol.* 31, 1307-1319.
11. Swartley, J. S., Liu, L. J., Miller, Y. K., Martin, L. E., Edupuganti, S., and Stephens, D. S. (1998) *J. Bacteriol.* 180, 1533-1539.
12. Pinner, R. W., Onyango, F., Perkins, B. A., Mirza, N. B., Ngacha, D. M., Reeves, M., DeWitt, W., Njeru, E., Agata, N. N., and Broome, C. V. (1992) *J. Infect. Diseases* 166, 359-364.
13. Zollinger, W. D., Boslego, J., Froholm, L. O., Ray, J. S., Moran, E. E., and Brandt, B. L. (1987) *Antonie Van Leeuwenhoek* 53, 403-411.
14. Janik, A., Juni, E., and Heym, G. A. (1976) *J. Clin. Microbiol.* 4, 71-81.
15. Dorsey, C. W., Tolmasky, M. E., Crosa, J. H., and Actis, L. A. (2003) *Microbiology* 149, 1227-1238.
16. Clark, V. L., Campbell, L. A., Palermo, D. A., Evans, T. M., and Klimpel, K. W. (1987) *Infect. & Immun.* 55, 1359-1364.
17. de Maagd, R. A., and Lugtenberg, B. (1986) *J. Bacteriol* 167, 1083-1085.
18. Finberg, K. E., Muth, T. R., Young, S. P., Maken, J. B., Heitritter, S. M., Binns, A. N., and Banta, L. M. (1995) *J. Bacteriol.* 177, 4881-4889.
19. Gotschlich, E. C., Liu, T. Y., and Artenstein, M. S. (1969) *J. Exp. Med.* 129, 1349-1365.
20. Dubois, M. (1956) *Anal. Chem.* 28, 350-356.
21. Reuhs, B. L., Carlson, R. W., and Kim, J. S. (1993) *J. Bacteriol.* 175, 3570-3580.
22. Stevenson, T. T., and Furneaux, R. H. (1991) *Carbohydr. Res.* 11, 195-211.
23. Karlyshev, A. V., Linton, D., Gregson, N. A., Lastovica, A. J., and Wren, B. W. (2000) *Mol. Microbiol.* 35, 529-541.
24. Kahler, C. M., Martin, L. E., Shih, G. C., Rahman, M. M., Carlson, R. W., and Stephens, D. S. (1998) *Infect. Immun.* 66, 5939-5947.
25. Hestrin, S. (1949) *J. Biol. Chem.* 180, 249-261.
26. Luthi, E., Love, D. R., McAnulty, J., Wallace, C., Caughey, P. A., Saul, D., and Bergquist, P. L. (1990) *Appl. Environ. Microbiol.* 56, 1017-1024.
27. Sau, S., Sun, J., and Lee, C. Y. (1997) *J. Bacteriol.* 179, 1614-1621.
28. Lernercinier, X., and Jones, C. (1996) *Carbohydr. Res.* 296, 83-96.
29. Jones, C., and Lernercinier, X. (2002) *J. Pharm. Biomed. Anal.* 30, 1233-1247.
30. Richmond, P., Borrow, R., Findlow, J., Martin, S., Thornton, C., Cartwright, K., and Miller, E. (2001) *Infect. Immun.* 69, 2378-2382.

31. Longworth, E., Fernsten, P., Mininni, T. L., Vogel, U., Claus, H., Gray, S., Kaczmarski, E., and Borrow, R. (2002) *FEMS. Immunol. Med. Microbiol.* 32, 119-123.
32. Richmond, P., Goldblatt, D., Fusco, P. C., Fusco, J. D., Heron, I., Clark, S., Borrow, R., and Michon, F. (1999) *Vaccine* 18, 641-646.
33. McNeely, T. B., Staub, J. M., Rusk, C. M., Blum, M. J., and Donnelly, J. J. (1998) *Infect. Immun.* 66, 3705-3710.
34. Franklin, M. J., and Ohman, D. E. (2002) *J. Bacteriol.* 184, 3000-3007.
35. Nivens, D. E., Ohman, D. E., Williams, J., and Franklin, M. J. (2001) *J. Bacteriol.* 183, 1047-1057.
36. Pier, G. B., Coleman, F., Grout, M., Franklin, M., and Ohman, D. E. (2001) *Infect. Immun.* 69, 1895-1901.
37. Bloemberg, G. V., J. E. Thomas-Oates, B. J. J. Lugtenberg, and H. P. Spaink. (1994) *Mol. Microbiol.* 11, 793-804.
38. Lopez-Lara, I. M., van den Berg, J. D., Thomas-Oates, J. E., Glushka, J., Lugtenberg, B. J., and Spaink, H. P. (1995) *Mol. Microbiol.* 15, 627-638.
39. Spaink, H. P., Sheeley, D. M., van Brussel, A. A., Glushka, J., York, W. S., Tak, T., Geiger, O., Kennedy, E. P., Reinhold, V. N., and Lugtenberg, B. J. (1991) *Nature* 354, 125-130.
40. Antignac, A., Ducos-Galand, M., Guiyoule, A., Pires, R., Alonso, J. M., and Taha, M. K. (2003) *Clin. Infect. Dis.* 37, 912-920.
41. Girardin, S. E., Travassos, L. H., Herve, M., Blanot, D., Boneca, I. G., Philpott, D. J., Sansonetti, P. J., and Mengin-Lecreulx, D. (2003) *J Biol Chem.* 278, 41702-41708.
42. Inohara, N., Ogura, Y., Fontalba, A., Gutierrez, O., Pons, F., Crespo, J., Fukase, K., Inamura, S., Kusumoto, S., Hashimoto, M., Foster, S. J., Moran, A. P., Fernandez-Luna, J. L., and Nunez, G. (2003) *J. Biol. Chem.* 278, 5509-5512.
43. Hindson, V. J., Moody, P. C., Rowe, A. J., and Shaw, W. V. (2000) *J. Biol. Chem.* 275, 461-466.
44. Hindson, V. J., Dunn, S. O., Rowe, A. J., and Shaw, W. V. (2000) *Biochim. Biophys. Acta* 1479, 203-213.
45. Lewendon, A., Ellis, J., and Shaw, W. V. (1995) *J. Biol. Chem.* 270, 26326-26331.
46. Denk, D., and Bock, A. (1987) *J. Gen. Microbiol.* 133 (Pt 3), 515-525.
47. Wigley, D. B., Derrick, J. P., and Shaw, W. V. (1990) *FEBS Lett.* 277, 267-271.
48. Hara, O., and Hutchinson, C. R. (1992) *J. Bacteriol.* 174, 5141-5144.
49. Luck, P. C., Freier, T., Steudel, C., Knirel, Y. A., Luneberg, E., Zahringer, U., and Helbig, J. H. (2001) *Int. J. Med. Microbiol.* 291, 345-352.
50. Slauch, J. M., Lee, A. A., Mahan, M. J., and Mekalanos, J. J. (1996) *J. Bacteriol.* 178, 5904-5909.
51. Verma, N. K., Brandt, J. M., Verma, D. J., and Lindberg, A. A. (1991) *Mol. Microbiol.* 5, 71-75.
52. Firmin, J. L., Wilson, K. E., Carlson, R. W., Davies, A. E., and Downie, J. A. (1993) *Mol. Microbiol.* 10, 351-360.
53. Bhasin, N., Albus, A., Michon, F., Livolsi, P. J., Park, J. S., and Lee, J. C. (1998) *Mol. Microbiol.* 27, 9-21.
54. Higa, H. H., and Varki, A. (1988) *J. Biol. Chem.* 263, 8872-8878.
55. Kroon, P. A., Williamson, G., Fish, N. M., Archer, D. B., and Belshaw, N. J. (2000) *Eur. J. Biochem.* 267, 6740-6752.
56. Yi, K., Stephens, D. S., and Stojiljkovic, I. (2003) *Infect. Immun.* 71, 1849-1855.
57. Hanahan, D. (1983) *J. Mol. Biol.* 166, 557-580.
58. Yanisch-Perron, C., Vieira, J., and Messing, J. (1985) *Gene* 33, 103-119.
59. Menard, R., Sansonetti, P. J., and Parsot, C. (1993) *J. Bacteriol.* 175, 5899-5906.
60. Tzeng, Y. L., Datta, A., Kolli, V. K., Carlson, R. W., and Stephens, D. S. (2002) *J. Bacteriol.* 184, 2379-2388.
61. Jennings, H. J., A. K. Bhattacharjee, D. R. Bundle, C. P. Kenny, A. Martin, and I. C. Smith. 1977. Journal of Infectious Diseases 136 Suppl:S78-83.
62. Stephens, D. S., L. H. Hoffman, and Z. A. McGee. 1983. J. Infect. Dis. 148:369-76.
63. Drogari-Apiranthitou, M., E. J. Kuijper, N. Dekker, and J. Dankert. 2002. Infect Immun 70:3752-8.
64. Filice, G. A., P. S. Hayes, G. W. Counts, J. M. Griffiss, and D. W. Fraser. 1985. J Clin Microbiol 22:152-6.
65. Amir, J., L. Louie, and D. M. Granoff. 2005. Vaccine 23:977-83.
66. Fattom, A. I., J. Sarwar, L. Basham, S. Ennifar, and R. Naso. 1998. Infect Immun 66:4588-92.
67. Orskov, F., I. Orskov, A. Sutton, R. Schneerson, W. Lin, W. Egan, G. E. Hoff, and J. B. Robbins. 1979. J Exp Med 149:669-85.
68. Szymanski C. M., Michael F. S., Jarrell H. C., et al. 2003. J. Biol. Chem. 278: 24509-20.
69. Gudlavalleti S. K., Datta A. K., Tzeng Y. L., Noble C., Carlson R. W., Stephens D. S. 2004. J. Biol. Chem. 279: 42765-73.

What is claimed is:

1. A method for acetylating Serogroup A polysaccharide prepared from *Neisseria meningitidis*, said method comprising the step of contacting an isolated serogroup A meningococcal capsular polysaccharide with an isolated Serogroup A *Neisseria meningitidis* O-acetyltransferase polypeptide comprising SEQ ID NO:2.

2. The method of claim 1 wherein the O-acetyltransferase polypeptide is encoded by an isolated polynucleotide sequence comprising SEQ ID NO:1.

3. An improved immunogenic composition comprising an acetylated capsular polysaccharide of *Neisseria meningitidis*, wherein the improvement comprises acetylation of the capsular polysaccharide according to the method of claim 1.

4. The immunogenic composition of claim 3 further comprising an adjuvant or cytokine.

5. A method for the O-acetylation of a meningococcal serogroup A capsular polysaccharide, the method comprising contacting a preparation comprising the meningococcal serogroup A capsular polysaccharide with an isolated Serogroup A *Neisseria meningitidis* O-acetyltransferase polypeptide comprising SEQ ID NO:2.

6. The method of claim 5, wherein the O-acetyltransferase polypeptide is encoded by an isolated polynucleotide sequence comprising SEQ ID NO:1.

7. An isolated acetylated meningococcal serogroup A capsular polysaccharide, wherein the isolated meningococcal serogroup A capsular polysaccharide has been acetylated according to the method of claim 5.

8. The isolated acetylated meningococcal serogroup A capsular polysaccharide of claim 7, wherein the acetylated meningococcal serogroup A capsular polysaccharide is 90-95% acetylated.

9. A composition comprising the isolated acetylated meningococcal serogroup A capsular polysaccharide of claim 7.

10. The composition of claim 9 further comprising an adjuvant or cytokine.

11. An acetylated capsular polysaccharide of *Neisseria meningitidis* serogroup A, wherein the O-3 and/or O-4 acetylation of the acetylated capsular polysaccharide of *Neisseria*

*meningitidis* serogroup A is increased over wild type *Neisseria meningitidis* serogroup A wherein the acetylation is performed by an O-acetyltransferase polypeptide comprising the sequence of SEQ ID NO:2.

12. An immunogenic composition comprising the acetylated capsular polysaccharide of *Neisseria meningitidis* serogroup A of claim 11.

13. The immunogenic composition of claim 12 further comprising an immunogenic carrier.

14. The immunogenic composition of claim 12 further comprising an adjuvant or cytokine.

15. A method for acetylating the O-3 and/or O-4 positions of an ($\alpha$1→6) linked N-acetyl-D-mannosamine-1-phosphate polymer, said method comprising the step of contacting an ($\alpha$1→6) linked N-acetyl-D-mannosamine-1-phosphate polymer with an O-acetyltransferase polypeptide comprising SEQ ID NO:2.

16. The method of claim 15 wherein the O-acetyltransferase polypeptide is encoded by an isolated polynucleotide sequence comprising SEQ ID NO:1.

17. An isolated acetylated ($\alpha$1→6) linked N-acetyl-D-mannosamine-1-phosphate polymer, wherein the isolated ($\alpha$1→6) linked N-acetyl-D-mannosamine-1-phosphate polymer has been acetylated according to the method of claim 15.

18. The isolated acetylated ($\alpha$1→46) linked N-acetyl-D-mannosamine-1 phosphate polymer of claim 17, wherein the acetylated ($\alpha$1→6) linked N-acetyl-D-mannosamine-1 phosphate polymer is 90-95% acetylated.

19. A composition comprising the isolated acetylated an ($\alpha$1→6) linked N-acetyl-D-mannosamine-1-phosphate polymer of claim 17.

20. The composition of claim 19 further comprising an adjuvant or cytokine.

* * * * *